United States Patent [19]

Yamashita et al.

[11] Patent Number: 5,556,943
[45] Date of Patent: Sep. 17, 1996

[54] CELL ADHESION PROTEIN, GENE CODING FOR THE SAME, PROCESS FOR PREPARING THE SAME AND CARRIER ONTO WHICH THE SAME IS IMMOBILIZED

[75] Inventors: Kenji Yamashita; Takaaki Ohara, both of Takasago; Hideo Niwa, Akashi; Fumio Osakada, Himeji; Takeshi Fukuchi; Tadahiro Edamura, both of Akashi; Tetsu Kakutani, Kakogawa, all of Japan

[73] Assignee: Kanegafuchi Kagaku Kogyo Kabushiki Kaisha, Osaka, Japan

[21] Appl. No.: 328,152

[22] Filed: Oct. 24, 1994

Related U.S. Application Data

[63] Continuation of Ser. No. 895,202, Jun. 5, 1992, abandoned.

[30] Foreign Application Priority Data

| | | | |
|---|---|---|---|
| Jun. 6, 1991 | [JP] | Japan | 3-134789 |
| Jun. 24, 1991 | [JP] | Japan | 3-151792 |
| Jun. 26, 1991 | [JP] | Japan | 3-154486 |
| Jul. 2, 1991 | [JP] | Japan | 3-161377 |
| Jul. 15, 1991 | [JP] | Japan | 3-173765 |
| Nov. 29, 1991 | [JP] | Japan | 3-315709 |

[51] Int. Cl.$^6$ .................... C07K 14/47; C07K 14/705
[52] U.S. Cl. .................... 530/350; 435/69.1; 435/70.1; 435/172.3; 435/252.3; 530/344
[58] Field of Search ............... 435/68.1, 69.1, 435/69.3, 70.1, 172.3, 252.3, 252.33; 530/305, 344, 350, 388.75, 825; 535/1, 11, 12

[56] References Cited

U.S. PATENT DOCUMENTS

| | | | |
|---|---|---|---|
| 4,956,281 | 9/1990 | Wallner et al. | 435/69.3 |
| 5,185,441 | 2/1993 | Wallner et al. | 536/23.5 |
| 5,223,394 | 6/1993 | Wallner | 435/6 |

FOREIGN PATENT DOCUMENTS

| | | |
|---|---|---|
| 19552/88 | 1/1989 | Australia . |
| 0268995 | 11/1987 | European Pat. Off. . |
| 268995 | 6/1988 | European Pat. Off. . |
| WO90/02181 | 3/1990 | WIPO . |
| WO91/13981 | 9/1991 | WIPO . |

OTHER PUBLICATIONS

Wallner et al, Journal of Experimental Medicine, vol. 166, 923–932, Oct. 1987.
Hünig et al, Nature, vol. 326, 298–301, 1987.
Journal of Immunology, vol. 141, No. 12, Dec. 15, 1988, Hollander et al., "Biosynthesis and Function of LFA–3 in Human Mutant Cells Deficient in Phosphatidylinositol–Anchored Proteins".
*Nature*, vol. 329, (Oct. 1987) pp. 840–842.
"Journal of Experimental Medicine," vol. 162 (1985), pp. 890–901.

*Primary Examiner*—Mary E. Mosher
*Assistant Examiner*—Laurie Scheiner
*Attorney, Agent, or Firm*—Armstrong, Westerman, Hattori, McLeland & Naughton

[57] ABSTRACT

A sheep LFA-3 protein and derivertires thereof, and derivertives of a human LFA-3 protein, gene coding for the proteins, and processes for preparing the proteins. Said proteins have high affinity for human T-cells.

8 Claims, 3 Drawing Sheets

```
                                          10                                          20
human  Phe Ser Gln Gln Ile Tyr Gly Val Val Tyr Gly Asn Val Thr Phe His Val Pro Ser Asn sheep  Val Ser Gln Asp Ile Tyr Gly Ala Met Asn Gly Asn Val Thr Phe Tyr Val Ser Glu Ser
                                      30                                          40
human  Val Pro Leu Lys Glu Val Leu Trp Lys Lys Gln Lys Asp Lys Val Ala Glu Leu Glu Asn sheep  Gln Pro Phe Thr Glu Ile Met Trp Lys Lys Gly Lys Asp Lys Val Val Glu Trp Asp Gln
                                              50
human  --- Ser Glu Phe Arg Ala Phe Ser Ser Phe Lys Asn Arg Val Tyr Ler Asp Thr Val Ser sheep  Thr Ser Gly Leu Glu Ala Phe Gln Ser Phe Lys Asn Arg Val His Leu Asp Ile Val Ser
       60                                      70
human  Gly Ser Leu Thr Ile Tyr Asn Leu Thr Ser Ser Asp Glu Asp Glu Tyr Glu Met Glu Ser sheep  Gly Asn Leu Thr Ile Thr Gly Leu Thr Lys Leu Asp Glu Asp Val Tyr Glu Ile Glu Ser
           80                                  90
human  Pro Asn Ile Thr Asp Thr Met Lys Phe Phe Leu Tyr Val Leu Glu Ser Leu Pro Ser Pro sheep  Pro Ser Val Lys Lys Ser Ser Gln Phe His Leu Arg Val Ile Glu Pro Pro Thr Pro
       100                                     110
human  Thr Leu Thr Cys Ala Leu Thr Asn Gly --- Ser Ile Glu Val Gln Cys Met Ile Pro Glu sheep  Ser Ala Ser Cys Phe Leu Thr Glu Gly Gly Asn Ile Thr Leu Thr Cys Ser Ile Pro Glu
           120                                     130
human  His Tyr Asn Ser His Arg Gly --- --- --- Leu Ile Met Tyr Ser Trp Asp Cys Pro Met sheep  Gly Asp Pro Lys Glu Leu Asp Asp Ser Asp Leu Ile Arg Tyr Leu Trp Glu Cys Pro Pro
                           140                                       150
human  --- Glu Gln Cys Lys Arg --- --- Asn Ser Thr Ser Ile Tyr Phe --- Lys Met Glu Asn sheep  Thr Ile Gln Cys His Arg Gly Ser Ile Ser --- Ser Glu Ala Phe Val Ser Ala Glu Ser
                                       160                                       170
human  Asp Leu Pro Gln Lys Ile Gln Cys Thr Leu Ser Asn Pro Leu Phe Asn Thr Thr Ser Ser sheep  Asp Leu Ser Gln Asn Val Gln Cys Ile Val Ser Asn Pro Leu Phe Arg Thr Ser Ala Ser
                                               180                                    190
human  Ile Ile Leu Thr Thr Cys Ile Pro Ser Ser Gly His Ser Arg His Arg Tyr Ala Leu Ile sheep  Val Ser Leu Ser Thr Cys Leu Pro --- Glu Asp Tyr Ala Arg His Arg --- --- --- ---
                                          200                                       210
human  Pro Ile Pro Leu Ala Val Ile Thr Thr Cys Ile Val Leu Tyr Met Asn Gly Ile Leu Lys sheep   --- --- --- --- --- --- --- --- --- --- --- --- --- --- --- --- --- --- --- ---
                                   220
human  Cys Asp Arg Lys Pro Asp Arg Thr Asn Ser Asn sheep  --- Phe Ser Gly Thr Ser
```

*FIG. 1*

```
                                          10                                              20
human  Phe Ser Gln Gln Ile Tyr Gly Val Val Tyr Gly Asn Val Thr Phe His Val Pro Ser Asn sheep  Val Ser Gln Asp Ile Tyr Gly Ala Met Asn Gly Asn Val Thr Phe Tyr Val Ser Glu Ser
                                          30                                              40
human  Val Pro Leu Lys Glu Val Leu Trp Lys Lys Gln Lys Asp Lys Val Ala Glu Leu Glu Asn sheep  Gln Pro Phe Thr Glu Ile Met Trp Lys Lys Gly Lys Asp Lys Val Val Glu Trp Asp Gln
                                                   50
human  ---Ser Glu Phe Arg Ala Phe Ser Ser Phe Lys Asn Arg Val Tyr Ler Asp Thr Val Ser sheep  Thr Ser Gly Leu Glu Ala Phe Gln Ser Phe Lys Asn Arg Val His Leu Asp Ile Glu Ser
           60                                      70
human  Gly Ser Leu Thr Ile Tyr Asn Leu Thr Ser Ser Asp Glu Asp Glu Tyr Glu Met Glu Ser sheep  Gly Asn Leu Thr Ile Thr Gly Leu Thr Lys Leu Asp Glu Asp Val Tyr Glu Ile Glu Ser
           80                                      90
human  Pro Asn Ile Thr Asp Thr Met Lys Phe Phe Leu Tyr Val Leu Glu Ser Leu Pro Ser Pro sheep  Pro Ser Val Lys Lys Ser Ser Gln Phe His Leu Arg Val Ile -------------
           100                                     110
human  Thr Leu Thr Cys Ala Leu Thr Asn Gly Ser Ile Glu Val Gln Cys Met Ile Pro Glu His sheep  -------------------------------------------
           120                                     130
human  Tyr Asn Ser His Arg Gly Leu Ile Met Tyr Ser Trp Asp Cys Pro Met Glu Gln Cys Lys sheep  -------------------------------------------
           140                                     150
human  Arg Asn Ser Thr Ser Ile Tyr Phe Lys Met Glu Asn Asp Leu Pro Gln Lys Ile Gln Cys sheep  -------------------------------------------
           160                                     170
human  Thr Leu Ser Asn Pro Leu Phe Asn Thr Thr Ser Ser Ile Ile Leu Thr Thr Cys Ile Pro sheep  -------------------------------------------
           180                                     190
human  Ser Ser Gly His Ser Arg His Arg Tyr Ala Leu Ile Pro Ile Pro Leu Ala Val Ile Thr sheep  ------Asp Tyr Ala Arg His Arg Tyr Val Leu Phe Ala Ile Leu Pro Ala Val Ile ---
           200                                     210
human  Thr Cys Ile Val Leu Tyr Met Asn Gly Ile Leu Lys Cys ------Asp Arg Lys Pro Asp sheep  --- Cys Gly Leu Leu Phe ------------Leu Lys Cys Phe Leu Gly Arg Arg Ser Gln
           220
human  Arg Thr Asn Ser Asn sheep  Arg Asn Ser Gly Pro
```

*FIG.2*

CELL ADHESION PROTEIN, GENE CODING FOR THE SAME, PROCESS FOR PREPARING THE SAME AND CARRIER ONTO WHICH THE SAME IS IMMOBILIZED

This application is a continuation of application Ser. No. 07/895,202 filed Jun. 5, 1992 now abandoned.

BACKGROUND OF THE INVENTION

The present invention relates to a novel cell adhesion protein, a gene coding for the same, a process for preparing the same and a carrier onto which the same is immobilized.

Forming rosette with sheep erythrocytes has been recognized to be one of specific responses of human T-cells. At present, it is understood that the forming rosette of sheep erythrocytes and human T-cells is a binding response due to high affinity of CD2 antigen receptor on a sheep erythrocyte for CD2 antigen on human T-cells (another name: T11 antigen). Any clear answer has not been obtained for the question why human T-cells form rosette with sheep erythrocytes easily. However, there is a possibility that in the structure of a sheep receptor for CD2 antigen itself there exists a function different from the function of human LFA-3, being a receptor for CD2 antigen in human. At present, it is known that the partly determined N-terminal amino acid sequence of a receptor on a sheep erythrocyte for CD2 antigen (SE0 ID NO:3) has about 50% homology with the amino acid sequence of human LFA-3, a receptor for CD2 antigen (refer to Unexamined Japanese Patent Publication No. 150228/1988). However, it is not known what kind of whole structure the receptor on sheep erythrocyte for CD2 antigen has. As to human LFA-3 molecule, it is known that the molecule is classified as a cell adhesion protein belonging to immunoglobulin superfamily (refer to A. F. Williams and A. N. Barclay, Annu. Rev. Immunol. 6, 381, (1988)) and that the molecule is constructed by, from N-terminus, immunoglobulin-like domain 1 (D 1 region), immunoglobulin-like domain 2 (D2 region), transmembrane region (TM region) and cytoplasm region (C region) (refer to B. P. Wallner et al., J. Exp. Med. 166, 923, (1987)). Further, there is also known human LFA-3 molecule which has D1 region and D2 region and binds to a membrane through glycosyl phosphatidylinositol (refer to B. Seed, Nature 329, 840, (1987)). Therefore, in the present specification, a CD2 antigen receptor having a structure of, from N-terminus, D1 region—D2 region—TM region—C region or a CD2 antigen receptor having D1 region and D2 region and binding to a membrane through glycosyl phosphatidylinositol is referred to as "LFA-3". A sheep receptor for CD2 antigen having unknown structure is kept to be referred to as a receptor for CD2 antigen.

A sheep receptor for CD2 antigen has various uses, such as a use as a reagent for detecting T-cells and a use as a ligand for separating T-cells from a mixture of various kinds of cells, because the receptor has high affinity for CD2 antigen of human T-cells. Further, it is known that CD2 antigen participates in various immune responses as functions of T-cells Therefore, a sheep receptor for CD2 antigen which has affinity for CD2 antigen can be used as an immunoregulative agent and more, as a therapeutic agent which targets a tumor of T-cell family or a leukemia cell by utilizing affinity thereof for T-cells.

A sheep receptor for CD2 antigen can be obtained from sheep erythrocytes. As a process for preparing a sheep receptor for CD2 antigen and a derivative of the receptor, there are known a process comprising solubilizing the receptor from sheep erythrocytes by a surfactant and purifying by an affinity-chromatography using antibodies therefore (refer to Unexamined Japanese Patent Publication No. 150228/1988) and a process comprising solubilizing the receptor from sheep erythrocytes by trypsin (refer to T. Kitao et al., J, Immunol. 117, 310, (1976)). However, a amount of the sheep receptor for CD2 antigen is very small on sheep erythrocytes and it is hard work to prepare a large amount of the sheep receptor for CD2 antigen for the above-mentioned uses.

At present, a protein which naturally exists in very small amount can be prepared inexpensively and in large amount by genetic engineering techniques. For preparing the sheep receptor for CD2 antigen by genetic engineering techniques, a necessary gene coding for the sheep CD2 antigen receptor has to be isolated (cloned) first. However, at present, a whole amino acid sequence of the sheep receptor for CD2 antigen is not known. Further, it is not known at all whether the sheep receptor for CD2 antigen is LFA-3 which is a CD2 antigen receptor having the structure of, from N-terminus, D1 region—D2 region—TM region—C region or a CD2antigen receptor having D1 region and D2 region and binding to a membrane through glycosyl phosphatidylinositol, or a receptor of other structures. Therefore, it has been impossible to detect a gene or mRNA coding for sheep LFA-3, to clone the sheep LFA-3 gene and to prepare sheep LFA-3 by genetic engineering techniques.

It can be considered that some processes can be used for cloning of sheep LFA-3 gene. For example, it may be possible, by using of DNA probe (mixed probe) which is deduced from the known N-terminal partial amino acid sequence of a sheep receptor for CD2 antigen (SEQ ID NO: 3) consisting of 29 amino acid residues, to screen a cDNA of sheep LFA-3 from a cDNA library derived from cells in which the sheep LFA-3 gene is expressed. However, the cDNA screened by the mixed DNA probe can not be certified to be a true gene coding for sheep LFA-3 unless the cDNA is sequenced. A mixed DNA probe is not appropriate for detecting for the sheep LFA-3 gene. A DNA probe which is designed and prepared according to the Lathe et al.'s method (refer to Lathe et al., J. Molec. Biol. 183, 1, 1985) is not always useful to clone a gene.

A monoclonal antibody for a sheep receptor for CD2 antigen has been obtained. It may be possible that cloning of the desired gene can be attained by using the antibody labeled by a radioactive substance to screen the gene from a gene expression library. However, there is no report wherein the monoclonal antibody can be really used for cloning.

Therefore, a sure means by which the sheep LFA-3 gene can be cloned has not been accomplished at present. A DNA probe which is useful for sure cloning of the sheep LFA-3 gene is a DNA probe which has the sequence of LFA-3 gene as it is. Such a DNA probe can selectively hybridize with the sheep LFA-3 gene or mRNA, therefore it is very useful to detect the LFA-3 gene or mRNA.

On the other hand, until now, there have not been known the existence of a LFA-3 like protein deficient in D2 region and a LFA-3 like protein deficient in TM region in sheep and also in humans. Such proteins have been first found in the present invention.

If these proteins have high affinity for CD2 antigen of human T-cells, it is considered that they are useful as a detecting reagent for human T-cells, as a ligand for separating T-cells of humans and the other animals, as an immunoregulative agent or as a therapeutic agent which targets tumors of T-cell family. For these uses, it is necessary to make a mass production of the protein possible. Although a process by genetic engineering techniques is appropriate for a mass production of such a protein, a gene coding for the protein has to be cloned and has to be analyzed in order to perform the process. Further, it is also necessary to search a protein which is more suitable for a process by genetic engineering techniques and to clone a gene coding for such a protein and to analyze the structure of the protein.

An object of the present invention is to provide a protein, which is appropriate for a process by genetic engineering techniques, having high affinity for CD2 antigen on human T-cells.

Another object of the present invention is to provide a gene coding for such a protein.

A further object of the present invention is to provide a process for preparing such a protein by genetic engineering techniques.

A still further object of the present invention is to provide a carrier onto which such a protein is immobilized.

These and the other objects of the present invention will become apparent from the description hereinafter.

SUMMARY OF THE INVENTION

In accordance with the present invention, there are provided a sheep LFA-3 protein, a sheep LFA-3 gene and a process for preparing sheep LFA-3, a LFA-3 like protein deficient in TM region, a LFA-3 like protein deficient in D2 region and a derivative of these proteins, a gene coding for the above-mentioned protein, a process for preparing the protein and a carrier onto which the protein is immobilized.

BRIEF EXPLANATION OF THE DRAWINGS

FIG. 1 is a figure in which the amino acid sequence of human LFA-3 (SEQ ID NO:8) is compared with the amino acid sequence of the sheep LFA-3 like protein deficient in TM region (SEQ ID NO: 36). Number in the figure represents number of amino acid from the N-terminus of human LFA-3. A symbol "-" represents deficiency of amino acid. A colon shown between is shown between homologous amino acids. TM region is underlined. As is clear from the figure, the sheep LFA-3 like protein deficient in TM region does not have the underlined sequence.

FIG. 2 is a figure in which the amino acid sequence of human LFA-3 (SEQ ID NO:8) is compared with the amino acid sequence of the sheep LFA-3 like protein deficient in D2 region (SEQ ID NO: 1). Number in the figure represents number of amino acid from the N-terminus of human LFA-3. A symbol "-" represents deficiency of amino acid. A colon is shown between homologous amino acids. D2 region is underlined. As is clear from the figure, the sheep LFA-3 like protein deficient in D2 region does not have the underlined sequence.

DETAILED DESCRIPTION

Figure 3:
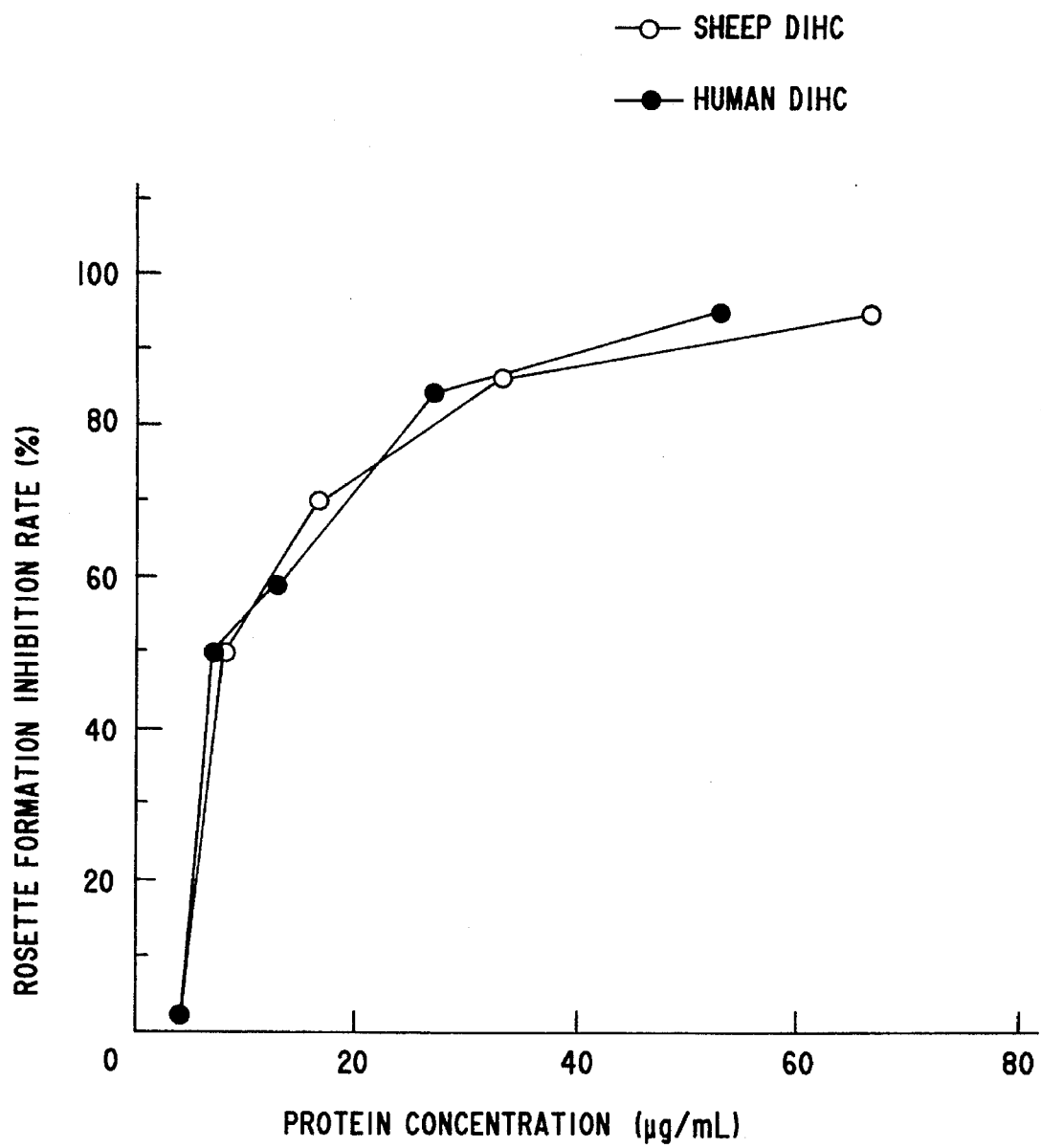
FIG. 3 is a graph showing rosette formation inhibition activity of the proteins of the present invention obtained in Example 4-r and Example 5-z respectively, that is, sheep D1HC protein and human D1HC protein.

A sheep LFA-3 protein is one of proteins of the present invention. The sheep LFA-3 protein is a CD2 antigen receptor derived from sheep having a structure of, from N-terminus, D1 region—D2 region—TM region—C region.

More particularly, the sheep LFA-3 protein comprises the amino acid sequence of SEQ ID NO: 31.

A gene coding for a sheep LFA-3 protein is one of genes of the present invention. More particularly, the sheep LFA-3 gene of the present invention codes for the amino acid sequence of SEQ ID NO: 31. The sheep LFA-3 gene of the present invention includes a gene which comprises the base sequence of SEQ ID NO:30.

The sheep LFA-3 gene of the present invention can be obtained as described below.

First, mRNA of sheep LFA-3 is prepared. The mRNA of sheep LFA-3 can be extracted from sheep cells or a sheep organ wherein a sheep LFA-3 gene has been expressed, such as leukocytes and hepatic cells. Firstly, RNA is extracted from such a material by means of a conventional method such as guanidine thiocyanate method or hot phenol method. From the extracted RNA, mRNA of sheep LFA-3 can be prepared as poly(A)$^+$RNA by means of an oligo(dT)-cellulose column (Rabomanyuaruidenshikogaku, edited by Masami Muramatsu, Maruzen, (1988)).

Second, cDNA of sheep LFA-3 is prepared from the obtained mRNA by means of a conventional method or a commercially available kit.

There are synthesized primers each of which is deduced from amino terminal sequence and carboxyl terminal sequence of the known partial amino acid sequence of a sheep receptor for CD2 antigen (SEQ ID NO: 3). With the synthesized primers, the above obtained cDNA is amplified by PCR (polymerase chain reaction) method (refer to Molecular Cloning 2nd edition, edited by J. Sambrook et al., Cold Spring Harbor Laboratory (1989); K. Knoth et al. (1988), Nucleic Acids Research, vol. 16, page 10932). The amplification by PCR method may be cycled suitable times to obtain a sufficient amount of cDNA for the following cloning. The amplified cDNA is detected by a conventional gel electrophoresis, e.g., polyacrylamide gel electrophoresis, and extracted.

Nucleotide sequence of the extracted DNA can be determined by inserting the DNA into a suitable vector such as pBR322, pUC18 or M13mp19, cloning the recombinant vector in a suitable host such as $E.\ coli$ JM109, and utilizing a conventional method, e.g. Sanger method or the like.

There can be used DNA having the determined DNA sequence of sheep LFA-3 as a probe useful for detection of the sheep LFA-3 gene and mRNA thereof. That is, a full-length cDNA of sheep LFA-3 can be easily detected from the sheep cDNA library by using the probe. Also, a full-length cDNA of sheep LFA-3 can be amplified by PCR method with the primers having thus determined sequence, and cloned. The cloned cDNA of sheep LFA-3 is characterized by analyzing with restriction enzymes or sequencing thereof.

Cloning of cDNA of sheep LFA-3 enables to produce sheep LFA-3 by genetic engineering techniques. As host, there can be used a bacterium such as $E.\ coli$ or Bacillus, a yeast, a fungus, a cultured cell of animal or plant, or the like.

The sheep LFA-3 protein of the present invention may have modified structure of the above-mentioned structure. Examples of the protein having the modified structure are, for instance, the proteins modified in dependence on a host cell which produces the protein, such as the protein wherein methionine residue is introduced at N-terminus of the protein due to production by using $E.\ coli$ as host and the protein modified with sugar due to production by using an animal cultured cell as host, and the like.

The LFA-3 like protein deficient in TM region is another protein of the present invention. The LFA-3 like protein deficient in TM region is a single polypeptide having the molecular weight of about 22,000 as protein which has structure of a LFA-3 protein lacking in TM region. "TM region" used herein means a region rich with hydrophobic amino acids contained in a membrane protein. The TM region in human LFA-3 protein is supposed to be the sequence from the 188th Tyr to the 212th Cys of SEQ ID NO:8. Also, the LFA-3 like protein deficient in TM region of the present invention includes polypeptides having a molecular weight higher than 22,000 with sugar chain.

The LFA-3 like protein deficient in TM region of the present invention may have modified structure of the above-mentioned structure. Examples of the protein having the modified structure are, for instance, the proteins modified in dependence on a host cell which produces the protein, such as the protein wherein methionine residue is introduced at N-terminus of the protein due to production by using E. coli as host and the protein modified with sugar due to production by using an animal cultured cell as host, and the like.

The LFA-3 like protein deficient in TM region has low molecular weight in comparison with the molecular weight of LFA-3, and does not have transmembrane region. Therefore, the protein of the present invention has low antigenicity and is a naturally occurring soluble LFA-3 like protein. The protein of the present invention is very advantageous to the production by genetic engineering techniques in comparison with LFA-3 being a membrane-binding protein by reason that the protein of the present invention can be secreted from animal cultured cells, yeasts and the like after production therein.

Then, there is explained the method for obtaining the gene coding for the LFA-3 like protein deficient in TM region of the present invention and the above-mentioned protein.

First, mRNA of the sheep LFA-3 like protein deficient in TM region is prepared. The mRNA of the sheep LFA-3 like protein deficient in TM region can be extracted from sheep cells or a sheep organ wherein a gene coding for the sheep LFA-3 like protein deficient in TM region has been expressed, such as leukocytes. Firstly, RNA is extracted from such a material by a conventional method such as guanidine thiocyanate method or hot phenol method. Then, from the extracted RNA, mRNA can be prepared as poly(A)$^+$RNA by means of an oligo(dT)-cellulose column (Rabomanyuaruidenshikogaku, edited by Masami Muramatsu, Maruzen, (1988)).

Second, cDNA of the sheep LFA-3 like protein deficient in TM region is prepared from the obtained mRNA by means of a conventional method or a commercially available kit.

There are synthesized mixed primers each of which is deduced from amino terminal sequence and carboxyl terminal sequence of the known partial amino acid sequence of a sheep receptor for CD2 antigen (SEQ ID NO:3). With the synthesized mixed primers, the above obtained cDNA is amplified by PCR method. The amplification by PCR method may be cycled suitable times to obtain a sufficient amount of cDNA for the following cloning. The amplified cDNA is detected by a conventional gel electrophoresis, e.g., polyacrylamide gel electrophoresis, and extracted.

Nucleotide sequence of the extracted DNA can be determined by inserting the DNA into a suitable vector such as pBR322, pUC18 or M13mp19, cloning the recombinant vector in a suitable host such as E. coli JM109, and utilizing a conventional method, e.g. Sanger method or the like.

There can be used DNA having the DNA sequence of the sheep LFA-8 like protein deficient in TM region determined as described above as a probe useful for detection of the gene coding for the sheep LFA-3 like protein deficient in TM region and mRNA thereof. That is, a full-length cDNA of the sheep LFA-3 like protein deficient in TM region can be easily detected by using the probe from the sheep cDNA library. Nucleotide sequence of the detected cDNA clone is determined. As a result, since the determined sequence has no DNA sequence coding for the sequence of TM region, the cDNA is characterized as the cDNA clone of the sheep LFA-3 like protein deficient in TM region.

The sheep LFA-3 like protein deficient in TM region can be obtained by inserting thus obtained full-length cDNA of the sheep LFA-3 like protein deficient in TM region or a DNA coding for the above-mentioned protein into a suitable expression vector, introducing the recombinant vector into a host cell suitable for the vector, for instance, a bacterium such as E. coli or Bacillus, a yeast, a fungus, a cultured cell of animal or plant or the like and culturing the transformed cell.

The cDNA of the human LFA-3 like protein deficient in TM region is screened as a clone which is selected with a probe having the nucleotide sequence of D1 region and is not selected with a probe having the nucleotide sequence of TM region, from cDNA library containing cDNA of the human LFA-3 like protein deficient in TM region; and cloned. Genes coding for a LFA-3 like protein deficient in TM region of animals other than human and sheep are selected as a cDNA having no DNA sequence coding for the sequence of TM region from cDNA clones which hybridize to the gene of the sheep LFA-3 like protein deficient in TM region or the gene of the human LFA-3 like protein deficient in TM region.

A LFA-3 like protein deficient in D2 region is a further protein of the present invention. The LFA-3 like protein deficient in D2 region is a single polypeptide having the molecular weight of about 15,000 as protein, which has structure of a LFA-3 protein lacking in D2 region and contains at most one disulfide bonding in the molecule. "D2 region" used herein means a region encoded by DNA which is segmented with introns from DNA encoding other regions on a genomic DNA, being the second immunoglobulin-like domain from N-terminus among two immunoglobulin-like domains of LFA-3 protein. The D2 regions in human and sheep have 6 cystein residues.

According to the present invention, it has been revealed that the LFA-3 like protein having D1 region and no D2 region shows higher affinity for CD2 antigen in comparison with LFA-3. Such fact has demonstrated that capacity for adhere to CD2 antigen in LFA-3 exists in not D2 region but D1 region. Therefore, it is considered that LFA-3 protein wherein there is (are) introduced variation(s) such as partial deficiency and/or substitution in D2 region, has the similar affinity to that of the LFA-3 like protein deficient in D2 region. Thus, the above-mentioned proteins having deficient D2 region are also included in the LFA-3 like protein deficient in D2 region of the present invention.

The LFA-3 like protein deficient in D2 region of the present invention may have modified structure of the above-mentioned structure. Examples of the protein having the modified structure are, for instance, the proteins modified in dependence on a host cell which produces the protein, such as the protein wherein methionine residue is introduced at N-terminus of the protein due to production by using E. coli as host and the protein modified with sugar due to production by using an animal cultured cell as host, and the like.

The LFA-3 like protein deficient in D2 region of the present invention has low molecular weight in comparison with the molecular weight of LFA-3. The protein of the present invention has at most one disulfide bonding whereas LFA-3 has plural disulfide bondings in the molecule. Therefore, the protein of the present invention is very advantageous by reasons of the low antigenecity and no possibility of forming a wrong disulfide bonding in production by genetic engineering techniques.

Hereinafter there is explained a derivative of the above-mentioned proteins deficient in D2 region, which is a still further protein produced according to the present invention. The derivative of the present invention includes soluble derivatives of the LFA-3 like protein deficient in D2 region which are proteins wherein variation(s) such as deficiency and/or substitution is (are) introduced in TM region rich with hydrophobic amino acids and/or C region thereof. The soluble derivative of the LFA-3 like protein deficient in D2 region is very advantageous to production by genetic engineering techniques by reason that the derivative can be secreted from an animal cultured cell, a yeast or the like after production therein. Also, because D1 region of human and sheep LFA-3 has no cysteine residue, there can be produced the derivative having no cysteine residue or the derivative having at most two cysteine residues according to the present invention. Such derivatives are very advantageous to production by genetic engineering techniques by reason of no possibility that a wrong disulfide bonding is formed.

From the derivative of the present invention wherein a few cysteine residues are introduced can be produced a carrier onto which the derivative is immobilized through the cysteine residue, a multimer and the derivative covalently bound with other substance. "D1 region" used herein means a region encoded by DNA which is segmented with an intron from the DNA encoding D2 region on a genomic DNA, being the immunoglobulin-like domain of N-terminus side among two immunoglobulin-like domains of LFA-3 protein.

Also, the derivative of the LFA-3 like protein deficient in D2 region of the present invention may have modified structure of the above-mentioned structure. Examples of the derivative having the modified structure are, for instance, the derivatives modified in dependence on a host cell which produces the derivative such as the derivative wherein methionine residue is introduced at N-terminus of the derivative due to production by using E. coli as host and the derivative modified with sugar due to production by using an animal cultured cell as host, and the like.

The gene coding for the LFA-3 like protein deficient in D2 region and the above-mentioned protein are prepared as described below.

First, mRNA of the sheep LFA-3 like protein deficient in D2 region is prepared. The mRNA of the sheep LFA-3 like protein deficient in D2 region can be extracted from sheep cells or a sheep organ wherein the gene of the sheep LFA-3 like protein deficient in D2 region has been expressed, such as leukocytes. Firstly, RNA is extracted from such a material by means of a conventional method such as guanidine thiocyanate method or hot phenol method. Then, from the extracted RNA, mRNA can be prepared as poly(A)+RNA by means of an oligo(dT)-cellulose column (refer to Rabomanyuaruidenshikogaku, edited by Masami Muramatsu, Maruzen, (1988)).

Second, cDNA of the sheep LFA-3 like protein deficient in D2 region is prepared from the obtained mRNA by means of a conventional method or a commercially available kit.

There are synthesized mixed primers each of which is deduced from amino terminal sequence and carboxyl terminal sequence of the known N-terminal 29 amino acid residues of the CD2 antigen receptor of sheep enythrocytes (SEQ ID NO:8). With the synthesized mixed primers, the above obtained cDNA is amplified by PCR method. The amplification by PCR method may be cycled suitable times to obtain a sufficient amount of cDNA for the following cloning. Thereby is amplified cDNA coding for N-terminal portion of the sheep LFA-3 like protein deficient in D2 region. The amplified cDNA is detected by a conventional gel electrophoresis, e.g., polyacrylamide gel electrophoresis, and extracted.

Nucleotide sequence of the extracted DNA can be determined by using a suitable vector such as pBR322, pUC18 or pUC19, cloning the vector in a suitable host such as E. coli and utilizing a conventional method, e.g., Sanger method or the like.

There can be used DNA having the determined DNA sequence of the sheep LFA-3 like protein deficient in D2 region as a probe useful for detection of the gene of the sheep LFA-3 like protein deficient in D2 region and mRNA thereof. That is, a full-length cDNA of the sheep LFA-3 like protein deficient in D2 region can be easily detected by using this probe from the cDNA library. The cloned full-length cDNA of the sheep LFA-3 like protein deficient in D2 region is characterized by analyzing with restriction enzymes or sequencing thereof. On the basis of the obtained nucleotide sequence of the gene, amino acid sequence of the sheep LFA-3 like protein deficient in D2 region is determined.

The sheep LFA-3 like protein deficient in D2 region can be obtained by inserting thus obtained cDNA of the sheep LFA-3 like protein deficient in D2 region into a suitable expression vector, introducing the recombinant vector into a host cell suitable for the vector, for instance, a bacterium such as E. coli or Bacillus, a yeast, a fungus, a cultured cell of animal or plant or the like and culturing the transformed cell.

Also, a soluble derivative of the sheep LFA-3 like protein deficient in D2 region can be prepared as a variant wherein variation(s) such as deficiency and/or substitution is (are) provided in the transmembrane region and/or the cytoplasm region whereas the amino acid sequence of D1 region is maintained, for instance, the derivative of the sheep LFA-3 like protein deficient in D2 region having an amino acid sequence wherein the sequence from the 1st amino acid to the 94th amino acid in SEQ ID NO: 1 is maintained and, in the sequence from the 95th amino acid to the 131st amino acid in SEQ ID NO: 1, a deficiency of at least one amino acid and/or a substitution of sequence exist(s).

The human LFA-3 like protein deficient in D2 region is obtained described below.

First, mRNA of the human LFA-3 like protein deficient in D2 region is prepared. The mRNA of the human LFA-3 like protein deficient in D2 region can be extracted from human cells or a human organ wherein the gene of the human LFA-3 like protein deficient in D2 region has been expressed, such as leukocytes or an established strain of human T-cells. Firstly, RNA is extracted from such a material by means of a conventional method such as guanidine thiocyanate method or hot phenol method. Then, from the extracted RNA, mRNA can be prepared as poly(A)+RNA by means of an oligo(dT)-cellulose column (refer to Rabomanyuaruidenshikogaku, edited by Masami Muramatsu, Maruzen, (1988)).

Second, cDNA of the human LFA-3 like protein deficient in D2 region is prepared from the obtained mRNA by means of a conventional method or a commercially available kit.

There are synthesized 5' primer and 3' primer coding for amino terminal sequence or carboxyl terminal sequence of the known amino acid sequence of human LFA-3 (SEQ ID NO:8). With the synthesized primers, the above obtained cDNA is amplified by PCR method. The amplification by PCR method may be cycled suitable times to obtain a sufficient amount of cDNA for the following cloning. The amplified cDNA is detected by a conventional gel electrophoresis, e.g., polyacrylamide gel electrophoresis, and extracted from the gel.

Nucleotide sequence of the extracted DNA can be determined by using a suitable vector such as pBR322, pUC18 or M13mp19, cloning the recombinant vector in a suitable host such as E. coli JM109, and using a conventional method, e.g. Sanger method or the like.

Also, the DNA of the human LFA-3 like protein deficient in D2 region is screened from the human cDNA library as a clone which is selected with a probe having the nucleotide sequence of D1 region and is not selected with a probe having the nucleotide sequence of D2 region; and cloned.

The cloned cDNA of the human LFA-3 like protein deficient in D2 region is characterized by analyzing with restriction enzymes or sequencing thereof.

The human LFA-3 like protein deficient in D2 region can be obtained by using a suitable expression vector and a host cell suitable for the vector, for instance, a bacterium such as E. coli or Bacillus, a yeast, a fungus, a cultured cell of animal or plant or the like and culturing the transformed cell.

A soluble derivative of the human LFA-3 like protein deficient in D2 region is prepared as a variant wherein variation(s) such as deficiency and/or substitution is (are) provided in the transmembrane region and/or the cytoplasm region whereas the amino acid sequence of D1 region is maintained, for instance, the derivative of the human LFA-3 like protein deficient in D2 region having an amino acid sequence wherein the sequence from the 1st amino acid to the 94th amino acid in SEQ ID NO: 13 is maintained and, in the sequence from the 95th amino acid to the 134th amino acid in SEQ ID NO: 13, a deficiency of at least one amino acid and/or a substitution exits(s); or the derivative of the human LFA-3 like protein deficient in D2 region having an amino acid sequence wherein the sequence from the 1st amino is acid to the 93rd amino acid in SEQ ID-NO: 13 is maintained and, in the sequence from the 94th amino acid to the 134th amino acid in SEQ ID NO:13, a deficiency of at least one amino acid and/or a substitution exist(s).

Genes coding for the LFA-3 like protein deficient in D2 region of animals other than human and sheep are selected from cDNA clones which hybridize to the gene of the sheep LFA-3 like protein deficient in D2 region or the gene of the human LFA-3 like protein deficient in D2 region, as cDNA having no DNA sequence coding for the sequence of D2 region.

By using thus obtained cDNA of the LFA-3 like protein deficient in D2 region of animals other than human and sheep, the protein corresponding to the selected cDNA and a derivative thereof can be obtained in the same manner as described above.

Further, the present invention has first revealed that a carrier onto which the LFA-3 like protein deficient in D2 region or a derivative thereof is immobilized can adsorb cells having CD2 antigen. It is found that the carrier onto which the LFA-3 like protein deficient in D2 region or the derivative thereof can selectively adsorb cells having CD2 antigen such as human T-cells and other animals T-cells. Also, adsorbed cells can be easily separated from the carrier with trypsin. Therefore, there can be utilized the carrier onto which the LFA-3 like protein deficient in D2 region or the derivative thereof for selective adsorption or separation of the T-cells.

As a carrier to be used for immobilization in the present invention, there can be used any of carriers onto which protein can be immobilized. Examples of the carrier to be used in the present invention are, for instance, plastic beads, plastic plates, plastic Schales and the like. The LFA-3 like protein deficient in D2 region or the derivative thereof can be immobilized by hydrophobic bonding, covalent bonding, ionic bonding or the like onto the carrier.

The whole amino acid sequence of sheep LFA-3 has been revealed by obtaining the cDNA of sheep LFA-3 of the present invention and determining the full-length base sequence thereof. According to the present invention, analysis and cloning of a sheep genomic LFA-3 gene are enabled. The sheep genomic LFA-3 gene is useful for genetic engineering production of sheep LFA-3 in an animal cultured cell as host whereas genomic DNA may contain introns.

In the genetic engineering production of sheep LFA-3, there can be produced not only molecules having the amino acid sequence of sheep LFA-3 which naturally occures, but also variants artificially bearing substitution, insertion and/ or deficiency of at least one amino acid and proteins combined with other protein. Also, chemically or enzymatically modified derivatives can be produced therefrom. Among the derivatives, there are contained derivatives having different affinity for CD2 antigen being a physiological ligand for LFA-3 from that of sheep LFA-3.

There can be used the sheep LFA-3 and variants thereof, or derivatives thereof produced by genetic engineering techniques which have affinity to human T-cells as diagnostic agents for T-cell detection. As the diagnostic agents can be utilized the above proteins labeled with an enzyme, a fluorescent agent or an isotope. Also, the produced sheep LFA-3, the variants and the derivatives which have affinity to T-cells, can be chemically or physically immobilized onto the carrier and subjected to separation (isolation or removal) of T-cells. Sheep LFA-3, the derivatives thereof and the proteins combined other protein are used as therapeutic agents which target a tumor of T-cell family or a leucemia cell by utilizing affinity thereof for T-cell. For instance, sheep LFA-3, the derivative thereof or the protein combined other protein, which is conjugated with a toxin such as ricin can be used as a therapeutic agent.

It is known that CD2 antigen being a natural ligand of LFA-3 participates in various immune responses as functions of T-cells. Therefore, sheep LFA-3, the variant thereof or the derivative thereof which has affinity for CD2 antigen can be utilized as an agent for inhibiting or activating immune response(s), i.e. an immunoregulative agent.

Further, according to the present invention there can be obtained the LFA-3 like protein deficient in TM region and the LFA-3 like protein deficient in D2 region, which are proteins having high affinity for CD2 antigen of human T-cells and are the LFA-3 like proteins suitable for production by genetic engineering techniques.

According to the present invention DNA coding for the above-mentioned proteins can be obtained. Therefore, the present invention enables to produce the LFA-3 like protein deficient in TM region and the LFA-3 like protein deficient in D2 region by genetic engineering techniques. Also, the present invention enables to produce not only the molecules having the amino acid sequence of naturally occurring LFA-3, but also variants bearing artificial substitution, insertion and/or deficiency of at least one amino acid in the amino acid sequence thereof and proteins combined with other protein. Also, the above-mentioned molecules, variants and the combined protein can be chemically or enzymatically modified to give derivatives. Thus obtained derivatives include the derivatives having different affinity for CD2 antigen being a natural ligand of LFA-3 from that of LFA-3.

There can be used as diagnostic agents T-cell detection the sheep LFA-3 protein, the LFA-3 like protein deficient in TM region, the LFA-3 like protein deficient in D2 region and derivatives thereof which are produced by genetic engineering techniques and have affinity to human T-cells. As the diagnostic agents, there can be utilized the above-mentioned proteins and derivatives thereof which are labeled with an enzyme, a fluorescent agent or an isotope. Also, the carrier of the present invention onto which at least one of them is chemically or physically immobilized can be subjected to separation (isolation or removal) of T-cells. There can be used the sheep LFA-3 protein, the LFA-3 like protein deficient in TM region, the LFA-3 like protein deficient in D2 region and derivatives thereof, and the proteins combined with other protein as therapeutic agents which target a tumor of T-cell family or a leucemia cell by utilizing affinity thereof for T-cells. For instance, the above-mentioned proteins, derivatives and the combined proteins which are conjugated with a toxin such as ricin, can be used as therapeutic agents.

It is known that CD2 antigen being a natural ligand of LFA-3 participates in various immune response as function of T-cell. Therefore, there can be utilized the sheep LFA-3 protein, the LFA-3 like protein deficient in D2 region, the LFA-3 like protein deficient in TM region, a variant thereof, or a derivative thereof which has affinity to CD2 antigen as an agent for inhibiting or activating immune response(s), i.e. an immunoregulative agent.

Also, comparing the amino acid sequence of the sheep LFA-3 like protein deficient in TM region with that of human LFA-3 (FIG. 1), it can be supposed that the human LFA-3 like protein deficient in TM region is a protein having a sequence wherein the sequence from the 188th amino acid to the 212th amino acid lacks in human LFA-3 of SEQ ID NO: 8, or a protein having a sequence wherein the sequence from the 188th amino acid to the 212th amino acid of human LFA-3 of SEQ ID NO: 8 lacks and further, in the sequence between the 213 th amino acid to the 222nd amino acid in SEQ ID NO: 8, at least one amino acid is substituted.

The present invention is more specifically described and explained by means of the following Examples in which all percents are by weight unless otherwise noted. It is to be understood that the present invention is not limited to the Examples, and various changes and modifications may be made in the invention without departing from the spirit and scope thereof.

EXAMPLE 1 a. Synthesis of primers used in polymerase chain reaction (PCR) for preparing cDNA of sheep LFA-3

As a partial amino acid sequence of a sheep S receptor for CD2 antigen, has been disclosed the N-terminal amino acid sequence consisting of 29 amino acid residues shown in SEQ ID NO: 3 (refer to Japanese Unexamined Patent Publication No. 150228/1988). In order to use in PCR for preparing cDNA coding for sheep LFA-3, following two kinds of mixed primers were synthesized by means of a DNA synthesizer (made by Applied Biosystems, Model 381A). One mixed primer is shown in SEQ ID NO: 4, consisting of a restriction enzyme BamHI recognition sequence and a following nucleotide sequence deduced from the sequence of the 1st–7th amino acids in SEQ ID NO:3. The other is shown in SEQ ID NO: 5, consisting of a sequence containing a restriction enzyme PstI recognition sequence and a following nucleotide sequence deduced from the sequence of the 27th–22nd amino acids in SEQ ID NO:3.

b. Preparation of double strand cDNA from sheep cells

From sheep was collected 100 ml of blood with heparin. The collected blood was centrifuged at 350G, 10 minutes to give a buffy coat fraction. After lysis of erythrocytes in the fraction by using erythrocyte lysing buffer, lysate was washed twice with PBS (phosphate buffered saline) to give sheep leukocytes. Then, from the obtained sheep leukocytes was extracted RNA by guanidine thiocyanate method. Further poly(A)$^+$RNA was purified by means of an oligo(dT)-cellulose column (refer to Rabomanyuaruidenshikogaku, edited by Masami Muramatsu, Maruzen, 1988). Double strand cDNA was synthesized from the poly(A)$^+$RNA by means of a commercially available kit (You-Prime cDNA Synthesis Kit #27-9260-01, made by Pharmacia). Similarly, another double strand cDNA was synthesized from a commercially available mRNA of sheep liver (made by Clontech).

c. Amplification by PCR method and cloning of cDNA coding for sheep LFA-3

By PCR method were amplified cDNA fragments coding for sheep LFA-3 vitro. That is, using 100 µl of a reaction mixture containing 10 mM Tris-HCl (pH 8.3), 100 mM potassium chloride, 1.5 mM magnesium chloride, 0.01% gelatin, 10 µM of each of 2 kinds of the mixed primers synthesized in the above-mentioned a, 10 ng of cDNA of the sheep leukocytes prepared in the above-mentioned b or cDNA of sheep liver, 0.2 mM of 4 kinds of deoxyribonucleic triphosphates (4 dNTP) and 2.5 units of Taq DNA polymerase, 35 cycles of PCR were carried out under the reaction condition per cycle of 94° C., 1 minute; 37° C., 2 minutes; and 72° C., 2 minutes. After completing the reactions, size of PCR products was measured by a polyacrylamide gel electrophoresis, and then it was found that DNA fragments of about 100 base pairs were amplified in both cases of using cDNA of sheep leukocyte and using cDNA of sheep liver. The DNA fragments of about 100 base pairs were extracted from the gel and treated with restriction enzymes BamHI and PstI. Then the treated DNA was inserted into BamHI-PstI site of M13mp19 phage vector (made by TAKARA SHUZO Co.) and cloned by using *E. coli* JM109 as host.

d. Sequencing of DNA amplified by PCR

There was determined sequence of the DNA of about 100 base pairs prepared from a positive clone obtained in the above-mentioned c by a conventional method using dideoxynucleotide triphosphates. As a result, both sequences between 2 kinds of the mixed primers used in PCR of PCR products from the leukocytes cDNA and the liver cDNA were determined to be the nucleotide sequence of the 19th–66th DNA sequence shown in SEQ ID NO: 30 (2 and 35). The sequence corresponds to the sequence from the 7th amino acid of Gly to the 22nd amino acid of Pro in the known partial amino acid sequence of a sheep receptor for CD2 antigen shown in SEQ ID NO: 3. It is shown that cDNA of sheep LFA-3 contains the above-mentioned nucleotide sequence. The DNA sequence codes the 7th–22nd amino acids in SEQ ID NO: 31 (1 and 36).

e. Isolation of cDNA of sheep LFA-3 and analogues thereof

In order to clone a full-length cDNA of sheep LFA-3, sheep cDNA library was screened by using N-terminal cDNA sequence of sheep LFA-3 determined in the above-mentioned d as a probe. That is, the double strand cDNA from sheep leukocytes prepared in the above-mentioned b was treated with DNA polymerase to give DNA fragments with blunt ends to which EcoRI linker (made by Pharmacia) was connected. Further, the linked DNA fragment was cut with EcoRI, and thereto were connected right and left arms of λgt11 (made by Stratagene) treated with alkaline phosphatase. Packaging in vitro was carried out to prepare cDNA library. There were synthesized probes having cDNA sequence adjacent N-terminus of sheep LFA-3, i.e., the probe having the nucleotide sequence of SEQ ID NO: 6 and that of SEQ ID NO: 7. By using these probes were screened about $2 \times 10^5$ recombinant phages. As a result, 3 positive done (SL-6, SL-40 and SL-43) containing 1.0 kb (kilonucleotide)-1.2 kb of cDNA insert were obtained.

EXAMPLE 2 f. Sequencing of cDNA of sheep LFA-3

Among the positive clones obtained in Example 1, cDNA contained in SL-6 was sequenced by dideoxy method using M13 phage. As a result, sequence shown in the nucleotide sequence of SEQ ID NO: 30 was found. Thus obtained nucleotide sequence corresponds to, and amino acid sequence determined from the nucleotide sequence is shown as, the amino acid sequence of sheep LFA-3 being the sequence from Val at N-terminus to Pro at C-terminus shown in SEQ ID NO:31. Comparison of the amino acid sequence of SEQ ID NO: 31 with that of human LFA-3 reveals that the determined amino acid sequence has regions corresponding to D1 region, D2 region, TM region and C region of human LFA-3, respectively. Therefore, it is confirmed that the protein encoded by thus obtained DNA is sheep LFA-3.

g. Construction of an expression vector for sheep LFA-3 protein in *E. coli*

In order to make cDNA coding for sheep LFA-3 protein express in *E. coli*, an expression vector was constructed. The DNA insert contained in the cDNA clone SL-6 obtained in Example 1 was taken out by cleaving with restriction enzyme EcoRI. The DNA insert was subcloned into EcoRI site of plasmid pUC18. Successively PCR was carried out by using the plasmid as a template. Used 5' primer is shown in SEQ ID NO: 37. This primer is comprised of BamHI recognition sequence, NcoI recognition sequence and the DNA sequence designed according to the sequence of the 1st–7th amino acids in SEQ ID NO: 31. Used 3' primer is shown in SEQ ID NO: 38. The primer is comprised of PstI recognition sequence, sequence of termination codon and the DNA sequence designed according to the sequence of the 219th–225th amino acids in SEQ ID NO: 31. PCR was carried out by using the primers of SEQ ID NO: 37 and SEQ ID NO: 38 to amplify DNA fragments. Thus amplified DNA fragments were cleaved with restriction enzymes BamHI and PstI, and thus obtained fragments were inserted into BamHI-PstI site of M13Mp 19 phage vectors. Nucleotide sequence of the inserted DNA was confirmed by dideoxy method. Then, DNA coding for sheep LFA-3 protein was taken out from the M13mp19 phage vector by cleaving with restriction enzymes NcoI and PstI. Thus obtained DNA was connected to NcoI-PstI site of vector pKK233-2 (made by Pharmacia) for expression to give an expression vector. Thus obtained expression vector is referred to as "pKSL".

h. Production of sheep LFA-3 protein by using *E. coli* as host

*E. coli* JM 109 (made by TAKARA SHUZO Co.) was precultured which has the expression vector pKSL of sheep LFA-3 protein. Then, the precultured *E coli* was inoculated in 100 ml of LB medium containing 10 mg of ampicilline, and shaking culture was carried out at 37° C. in 500 ml of Sakaguchi flask until absorbance at 600 nm (hereinafter referred as "$A_{600}$") of the medium containing *E. coli* became 0.3. Successively thereto was added IPTG (isopropyl-β-D-thio-galactopyranoside, made by Wako Pure Chemical Industries, Ltd.) so as to give a final concentration of 1 mM and further culture was continued for 6 hours. The cultured cells were collected by centrifugation, and suspended in 10 ml of 50 mM Tris-HCl buffer (pH 8.0) containing 50 mM EDTA, 5 Triton X-100 and 8% sucrose. Thereto was added lysozyme so as to give a final concentration of 0.1%. The cell suspension was sonicated and centrifuged to give an insoluble precipitation fraction. The obtained precipitation was washed with 50% glycerol and successively with ethanol to give inclusion bodies containing produced sheep LFA-3 protein. The inclusion bodies were dissolved with SDS (sodium dodecyl sulfate) and subjected to SDS-polyacrylamide gel electrophoresis to detect a band of molecular weight 25,000–27,000.

EXAMPLE 3 i. Sequencing of cDNA of the sheep LFA-3 like protein deficient in TM region (hereinafter referred as to "sheep A TM protein")

Among the positive clones obtained in Example 1, cDNA contained in SL-43 was sequenced by dideoxy method using M13 phage. As a result, sequence shown in the nucleotide sequence of SEQ ID NO: 35. Thus obtained nucleotide sequence corresponds to, and amino acid sequence determined from the nucleotide sequence is shown as, the amino acid sequence of sheep ΔTM protein being the sequence from Val at N-terminus to Ser at C-terminus shown in SEQ ID NO: 36. The sequencing also revealed that sheep ΔTM protein has a signal peptide having 28 amino acid residues which starts from methionine. On the basis of thus obtained information of cDNA and nucleotide sequence of sheep ΔTM protein, natural type sheep A TM protein and a derivative thereof can be produced with a recombinant by genetic engineering techniques. FIG. 1 shows comparison of the amino acid sequence of sheep ΔTM protein shown in SEQ ID NO: 13 to that of human LFA-3 shown in SEQ ID NO: 8. FIG. 1 reveals that sheep ΔTM protein lacks TM region (underlined portion) existing in human LFA-3. (underlined portion) existing in human LFA-3.

j. Preparation of an expression vector of sheep ΔTM protein in *E. coli*

In order to make cDNA coding for sheep ΔTM protein express in *E. coli*, an expression vector was constructed. The DNA insert contained in the cDNA clone SL-43 obtained in Example 1 was taken out by cleaving with restriction enzyme EcoRI. The DNA insert was subcloned into EcoRI site of plasmid pUC18. Successively such plasmid was subjected to PCR. Used 5' primers are shown in SEQ ID NO: 32 and 33. These primers are comprised of BamHI recognition sequence, NcoI recognition sequence and the DNA sequence designed according to the sequence of the 1st–7th amino acids in SEQ ID NO: 36. Used 3' primer is shown in SEQ ID NO: 34. The primer is comprised of SalI recognition sequence, PstI recognition sequence, sequence of termination codon and the DNA sequence designed according to the sequence of the 199th–193rd amino acids in SEQ ID NO: 36. PCR was carried out by using the primers of SEQ ID NO: 32 and 34, or the primers of SEQ ID NO: 33 and 34 to amplify DNA fragments. Thus amplified DNA fragments were cleaved with restriction enzymes BamHI and SalI, and thus obtained fragments were inserted into each BamHI-SalI site of M13mp19 phage vector. Nucleotide sequence of the inserted DNA was confirmed to have the desired sequence by dideoxy method. Then, DNA of sheep ΔTM protein was taken out from the M13mp19 phage vectors by cleaving with restriction enzymes NcoI and PstI. Thus obtained DNAs were connected to NcoI-PstI site of vector pKK 233-2 made by Pharmacia) for expression to give two expression vectors. One of thus obtained expression vector is referred to as "pKSLΔTM-0", which was prepared by using the primers of SEQ ID NO: 32 and 34. The other is referred to as "pKSLΔTM-1", which was prepared by using the primers of SEQ ID NO: 33 and 34.

k. Production of sheep ΔTM protein by using E. coli as host

E. coli JM 109 (made by TAKARA SHUZO Co.) was precultured which has the expression vector pKSLΔTM-0 or pKSLΔTM-1 of sheep ΔTM protein. Then, the precultured E. coli was inoculated in 100 ml of LB medium containing 10 mg of ampicilline, and shaking culture was carried out at 37° C. in 500 ml of Sakaguchi flask until $A_{600}$ of the medium containing E. coli became 0.3. Successively thereto was added IPTG so as to give a final concentration of 1 mM and further culture was continued for 6 hours. The cultured cells were collected by centrifugation, and suspended in 10 ml of 50 mM Tris-HCl buffer (pH 8.0) containing 50 mM EDTA, 5% Triton X-100 and 8% sucrose. Thereto was added lysozyme so as to give a final concentration of 0.1%. The cell suspension was sonicated, and centrifuged to give an insoluble precipitation fraction. The obtained precipitation was washed with 50% glycerol and successively with ethanol to give inclusion bodies containing produced sheep ΔTM protein. The expression vector pKSLΔTM-1 was superior to the expression vector pKSLΔTM-0 in productivity. The inclusion bodies were dissolved with SDS (sodium dodecyl sulfate) and subjected to SDS-polyacrylamide gel electrophoresis to detect a band of apparent molecular weight 23,000–25,000.

l. Solubilization and renaturation of inclusion bodies containing sheep ΔTM protein All the inclusion bodies obtained in the above-mentioned k were dissolved in 10 ml of a buffer (pH 9.5) containing 8M urea, 20 mM ammonium acetate, 0.4 mM cystein and 0.04 mM cystein and centrifuged to give a supernatant. The supernatant was diluted with 8M urea so as to become $A_{280}$ 0.1, and dialyzed against ten-fold amount of the same buffer and successively against PBS to give a solution containing soluble sheep ΔTM protein. Thus obtained protein was subjected to SDS-polyacrylamide gel electrophoresis to detect a band of molecular weight 23,000–25,000. The molecular weight also confirmed that the obtained protein is sheep ΔTM protein. Thus prepared sheep ΔTM protein in an amount ranging from 25–0 μg was mixed with $1\times10^5$ Jurkat cells which were washed with the PBS containing 5% bovine serum albumin (BSA) and 1% glucose, and contained in 50 μl of the same buffer. Thereafter there was observed effect on rosette formation by adding $1\times10^7$ sheep erythrocytes. Sheep ΔTM protein dose-dependently inhibited the rosette formation of Jurkat cells with sheep erythrocytes.

With respect to sheep ΔTM protein, the concentration for inhibiting 50% rosette formation was about 20 μg/ml.

EXAMPLE 4 m. Sequencing of cDNA of the sheep LFA-3 like protein deficient in D2 region (hereinafter referred to as "sheep ΔD2 protein")

Among the positive clones obtained in Example 1, cDNA sequence contained in SL-40 was determined by dideoxy method using M13 phage. As a result, it is revealed that sheep ΔD2 protein is encoded by the nucleotide sequence of SEQ ID NO: 2 and has the amino acid sequence of SEQ ID NO: 1. It is also revealed that sheep ΔD2 protein has a signal peptide having 28 amino acid residues which starts from methionine. On the basis of thus obtained information of cDNA of sheep ΔD2 protein, natural type sheep ΔD2 protein and derivatives thereof can be produced by genetic engineering techniques. The amino acid sequence of SEQ ID NO: 8 is that of human LFA-3 which has been reported by Wallner et al (B. P. Wallner et at., Journal of Experimental Medicine, vol. 166, p 923, (1987)), and SEQ ID NO: 16 shows the DNA sequence thereof. Also, FIG. 2 shows correspondence of the amino acid sequence of sheep ΔD2 protein shown in SEQ ID NO: 1 to that of human LFA-3 shown in SEQ ID NO: 8. FIG. 2 reveals that sheep ΔD2 protein lacks D2 region (underlined portion) existing in human LFA-3.

n. Preparation of an expression vector of sheep ΔD2 protein in E. coli

In order to make cDNA coding for sheep ΔD2 protein express in E. coli, an expression vector was constructed. The DNA insert contained in the cDNA clone SL-40 obtained in Example 1 was taken out by cleaving with restriction enzyme EcoRI. The DNA fragment was subcloned into EcoRI site of plasmid pUC18. Successively such plasmid was subjected to PCR. Used 5' primer is shown in SEQ ID NO: 9. This primer is comprised of BamHI recognition sequence, NcoI recognition sequence and the DNA sequence designed according to the sequence of the 1st–7th amino acids of SEQ ID NO: 2. Used 3' primer is shown in SEQ ID NO: 10. The primer is comprised of SaiI recognition sequence, PstI recognition sequence, sequence of termination codon and the DNA sequence designed according to the sequence of the 131st–126th amino acids of SEQ ID NO: 2. PCR was carried out by using the primers of SEQ ID NO: 9 and SEQ ID NO: 10 to amplify DNA fragments. Thus amplified DNA fragments were cleaved with restriction enzymes BamHI and SalI, and thus obtained fragments were inserted into BamHI-SalI site of M13 mp 19 phage vector. Nucleotide sequence of the inserted DNA was confirmed by dideoxy method. Then, DNA coding for sheep A D2 protein was taken out from the M13mp19 phage vector by cleaving with restriction enzymes NcoI and PstI. Thus obtained DNA was connected to NcoI-PstI site of vector pKK233-2 (made by Pharmacia) for expression to give an expression vector. Thus obtained expression vector is referred to as "pKSLΔD2". SEQ ID NO: 20 shows nucleotide sequence from initiation codon to termination codon coding for sheep ΔD2 protein contained in pKSLΔD2.

o. Production of sheep ΔD2 protein by using E. coli as host

E. coli JM 109 (made by TAKARA SHUZO Co.) was precultured which has the expression vector pKSLΔD2 of sheep ΔD2 protein. Then, the precultured E. coli was inoculated in 100 ml of LB medium containing 10 mg of ampicilline, and shaking culture was carried out at 37° C. in 500 ml of Sakaguchi flask until $A_{600}$ of the medium containing E. coli became 0.3. Successively thereto was added IPTG so as to give a final concentration of 1 mM and further culture was continued for 6 hours. The cultured cells were collected by centrifugation, and suspended in 10 ml of 50 mM Tris-HCl buffer (pH 8.0) containing 50 mM EDTA, 5% Triton X-100 and 8% sucrose. Thereto was added lysozyme so as to give a final concentration of 0.1%. The cell suspension was sonicated, and centrifuged to give an insoluble precipitation fraction. The obtained precipitation was washed with 50% glycerol and successively with ethanol to give inclusion bodies containing produced sheep ΔD2 protein. The inclusion bodies were dissolved with SDS and subjected to SDS-polyacrylamide gel electrophoresis to detect a band of molecular weight 15,000–16,000.

p. Preparation of an expression vector of a soluble derivative of sheep ΔD2 protein (hereinafter referred to as "sheep D1HC protein") in *E. coli*

In order to make cDNA of sheep D1HC protein express in *E. coli*, an expression vector was constructed.

Namely, the DNA insert contained in the cDNA clone SL-40 obtained in Example 1 was taken out by cleaving with restriction enzyme EcoRI. The DNA insert was subcloned into EcoRI site of plasmid pUC18. Successively such plasmid was subjected to PCR. Used 5' primer is shown in SEQ ID NO: 9. This primer is comprised of BamHI recognition sequence, NcoI recognition sequence and the DNA sequence designed according to the sequence of the 1st–7th amino acids of SEQ ID NO: 2. Used 3' primer is shown in SEQ ID NO: 11. The primer is comprised of PstI recognition sequence, sequence of termination codon, the 371st–3581h nucleotide sequence and the 301st–2771h nucleotide sequence of SEQ ID NO: 2. PCR was carried out by using the primers of SEQ ID NO: 9 and SEQ ID NO: 11 to amplify DNA fragments. Thus amplified DNA fragments were cleaved with restriction enzymes BamHI and PstI, and thus obtained fragments were inserted into BamHI-PstI site of M13mp19 phage vectors. Nucleotide sequence of the inserted DNA was confirmed by dideoxy method. Then, DNA of sheep D1HC protein was taken out from the M13mp19 phage vector by cleaving with restriction enzymes NcoI and PstI. Thus obtained DNA was connected to NcoI-PstI site of vector pKK233-2 (made by Pharmacia) for expression to give an expression vector. Thus obtained expression vector is referred to as "pKSLD1HC". SEQ ID NO: 21 shows nucleotide sequence from initiation codon to termination codon coding for sheep D1HC protein contained in pKSLD1HC.

q. Production of sheep D1HC protein by using *E. coli* as host

*E. coli* JM 109 (made by TAKARA SHUZO Co.) was precultured which has the expression vector pKSLD1HC of sheep D1HC protein. Then, the precultured *E. coli* was inoculated in 100 ml of LB medium containing 10 mg of ampicilline, and shaking culture was carried out at 37° C. in 500 ml of Sakaguchi flask until $A_{600}$ of the medium containing *E. coli* became 0.3. Successively thereto was added IPTG so as to give a final concentration of 1 mM and further culture was continued for 6 hours. The cultured cells were collected by centrifugation, and suspended in 10 ml of 50 mM Tris-HCl buffer (pH 8.0) containing 50 mM EDTA, 5% Triton X-100, 2 mM dithiothreitol and 8% sucrose. Thereto was added lysozyme so as to give a final concentration of 0.1%. The cell suspension was sonicated, and centrifuged to give insoluble inclusion bodies. The inclusion bodies were dissolved with SDS and subjected to SDS-polyacrylamide gel electrophoresis to detect a band of molecular weight about 12,000.

r. Solubilization and renaturation of inclusion bodies containing sheep D1HC protein All the inclusion bodies obtained in the above-mentioned q were dissolved in 10 ml of 50 mM Tris-HCl buffer (pH 7.4) containing 6M guanidine chloride and 2 mM EDTA, and centrifuged to give a supernatant. The supernatant was dialyzed against PBS to give a solution containing sheep D1HC protein. Thus prepared sheep D1HC protein was mixed with $1 \times 10^5$ Jurkat cells which were washed with PBS containing 5% bovine serum albumin (BSA) and 1% glucose, and contained in 50 μl of the same buffer. There-after there was observed effect on rosette formation by adding $.1 \times 10^7$ sheep erythrocytes. Sheep D1HC protein dose-dependently inhibited the rosette formation of Jurkat cells with sheep erythrocytes. The results are shown in FIG. 3.

Rosette formation inhibition rate was calculated by the following formula;

$$\text{Inhibition rate (\%)} = 1 - \frac{\text{Rosette positive cells (\%) in sample}}{\text{Rosette positive cells (\%) in control}} \times 100$$

"Rosette positive cells" are cells to which not less than 5 sheep erythrocytes per cell adhere to form rosette.

EXAMPLE 5 s. Synthesis of primers used in PCR for preparing cDNA of the human LFA-3 like protein deficient in D2 region (hereinafter referred to as "human ΔD2 protein")

There was cloned cDNA of human LFA-3, and the nucleotide sequence thereof has been known (B. P. Wallner et al., Journal. of Experimental Medicine, vol. 166, p 923, (1987)). The nucleotide sequence is shown in SEQ ID NO: 16. In order to use in PCR for preparing cDNA coding for human ΔD2 protein, following 2 kinds of primers were synthesized by means of a DNA synthesizer (made by Applied Biosystems, Model 381A). One was a primer, shown in SEQ ID NO: 14, consisting of a sequence containing the recognition sequences of restriction enzymes PstI and NcoI and the 1st–24 th nucleotide sequence of SEQ ID NO: 16. The other was a primer, shown in SEQ ID NO: 15, consisting of a sequence containing the recognition sequences of restriction enzymes PstI and EcoRI and the 753rd–730th nucleotide sequence of SEQ ID NO: 16.

t. Preparation of cDNA of human ΔD2 protein

Human T-cell line MOLT-4 (ATCC CRL-1582) was cultured in RPMI 1640 medium containing 10% fetal calf serum (FCS) to give $5 \times 10^8$ cells. The cells were washed twice with PBS. Successively RNA was extracted from the cells by guanidine thiocyanate method. Further poly(A)+ RNA was purified by means of an oligo(dT)cellulose column (refer to Rabomanyuaruidenshikogaku, edited by Masami Muramatsu, Maruzen, (1988)). Double strand cDNA was synthesized from the poly(A)+RNA by means of a commercially available kit (cDNA synthesis kit #27-9260-01, made by Pharmacia).

u. Amplification by PCR method and cloning of cDNA coding for human ΔD2 protein, and sequencing thereof By PCR method were amplified cDNA fragments coding for human ΔD2 protein in vitro. That is, using 100 μl of a reaction mixture containing 10 mM Tris-HCl (pH 8.3), 100 mM potassium chloride, 1.5 mM magnesium chloride, 0.01% gelatin, 10 μM of each of 2 kinds of primers synthesized in the above-mentioned s, 10 ng of human double strand cDNA prepared in the above-mentioned t, 0.2 mM of 4 kinds of deoxyribonucleic triphosphates (4 dNTP) and 2.5 units of Taq DNA polymerase, 35 cycles of PCR were carried out under the reaction condition per cycle of 94° C., 1 minute; 37° C., 2 minutes; and 72° C., 2 minutes. After completing the reactions, size of PCR products was measured by a polyacrylamide gel electrophoresis, and then it was found that DNA fragments of about 500 base pairs were amplified. The DNA fragments of about 500 base pairs were extracted from the gel and treated with restriction enzyme PstI. Then the treated DNA was inserted into PstI site of pUC19 vector (made by TAKARA SHUZO Co.) and cloned by using *E. coli* JM109 as host. The prepared plasmid is referred to as "pHLΔD2".

Then, in order to sequence cDNA amplified by PCR, the DNA fragment of about 500 base pairs cleaved with PstI was inserted into PstI site of M13mp19 phage vector (made by TAKARA SHUZO Co.) and sequenced by a conventional method using dideoxynucleotide triphosphates. As a result, cDNA sequence of human ΔD2 protein shown in SEQ ID NO: 12 was found among about 500 base pairs of DNA fragments. Such cDNA sequence codes for the protein having the amino acid sequence shown in SEQ ID NO: 13. Comparing human ΔD2 protein shown in SEQ ID NO: 13 with human LFA-3 shown in SEQ ID NO: 8, it is found that human ΔD2 protein lacks the amino acids from the 94th amino acid of Glu to the 181st amino acid of Ser in SEQ ID No: 8, i.e., D2 region.

v. Preparation of an expression vector of human ΔD2 protein in *E. coli*

In order to make cDNA of human ΔD2 protein express in *E. coli*, an expression vector was constructed. The DNA of plasmid pHLΔD2 having cDNA of human ΔD2 protain obtained in the above-mentioned u was used as a template to carry out PCR. Used 5' primer is shown in SEQ ID NO: 17. This primer is comprised of KpnI recognition sequence, GG, sequence of initiation codon and the 1st–241th nucleotide sequence of SEQ ID No: 12. Used 3' primer is shown in SEQ ID NO: 18. The primer is comprised of HindIII recognition sequence, NheI recognition sequence, sequence of termination codon and the 402nd–379th nucleotide sequence of SEQ ID NO: 12. PCR was carried out by using the primers of SEQ ID NO: 17 and SEQ ID NO: 18 to amplify DNA fragments. Thus amplified DNA fragments were cleaved with restriction enzymes KpnI and HindIII. The cleaved fragments were connected to KpnI-HindIII site of vector pKK233Kpn to give an expression vector. Thus obtained expression vector is referred to as "pKHLΔD2". The vector pKK233Kpn is a plasmid wherein the sequence from SD sequence to initiation codon AGGAAACAGACCATG of pKK233-2 (made by Pharmacia) has been varied to the sequence AGGAGGTACCGGATG containing the recognition sequence of restriction enzyme KpnI by site directed mutagenesis method. SEQ ID NO: 22 shows the nucleotide sequence from initiation codon to termination codon coding for human ΔD2 protein contained in pKHLΔD2.

w. Production of human ΔD2 protein by using *E. coli* as host

*E. coli* JM 109 (made by TAKARA SHUZO Co.) was precultured which has the expression vector pKHLΔD2 of human ΔD2 protein. Then, the precultured *E. coli* was inoculated in 100 ml of LB medium containing 10 mg of ampicilline, and shaking culture was carried out at 37° C. in 500 ml of Sakaguchi flask until $A_{600}$ of the medium containing *E. coli* became 0.3. Successively thereto was added IPTG so as to give a final concentration of 1 mM and further culture was continued for 6 hours. The cultured cells were collected by centrifugation, and suspended in 10 ml of 50 mM Tris-HCl buffer (pH 8.0) containing 50 mM EDTA, 5% Triton X-100 and 8% sucrose. Thereto was added lysozyme so as to give a final concentration of 0.1%. The cell suspension was sonicated, and centrifuged to give an insoluble precipitation fraction. The obtained precipitation was washed with 50% glycerol and successively with ethanol to give inclusion bodies containing produced human ΔD2 protein. The inclusion bodies were dissolved with SDS and subjected to SDS-polyacrylamide gel electrophoresis to detect a band of molecular weight 15,000–16,000.

x. Preparation of an expression vector of a soluble derivative of human ΔD2 protein (hereinafter referred to as "human D1HC protein") in *E. coli*

In order to make cDNA of human D1HC protein express in *E. coli*, an expression vector was constructed.

That is, the DNA of plasmid pHLΔD2 having cDNA of human ΔD2 protein obtained in the above-mentioned u was used as a template to carry out PCR. Used 5' primer is shown in SEQ ID NO: 17. This primer is comprised of KpnI recognition sequence, GG, sequence of initiation codon and the 1st–241th nucleotide sequence of SEQ ID No: 12. Used 3' primer is shown in SEQ ID NO: 19. The primer is comprised of HindIII recognition sequence, sequence of termination codon and the 402nd–373rd nucleotide sequence and the 2971th–268th nucleotide sequence of SEQ ID NO: 12. PCR was carried out by using the primers of SEQ ID NO: 17 and SEQ ID NO: 19 to amplify DNA fragments. Thus amplified DNA fragments were cleaved with restriction enzymes KpnI and HindIII. The cleaved fragments were connected to KpnI-HindIII site of vector pKK233Kpn to give an expression vector. Thus obtained expression vector is referred to as "pKHLD1HC". SEQ ID NO: 23 shows the nucleotide sequence from initiation codon to termination codon coding for human D1HC protein contained in pKHLD1HC.

y. Production of human D1HC protein by using *E. coli* as host

*E. coli* JM 109 (made by TAKARA SHUZO Co.) was precultured which has the expression vector pKHLD1HC of human D1HC protein. Then, the precultured *E. coli* was inoculated in 100 ml of LB medium containing 10 mg of ampicilline, and shaking culture was carried out at 37° C. in 500 ml of Sakaguchi flask until $A_{600}$ of the medium containing *E. coli* became 0.3. Successively thereto was added IPTG so as to give a final concentration of 1 mM and further culture was continued for 6 hours. The cultured cells were collected by centrifugation, and suspended in 10 ml of 50 mM Tris-HCl buffer (pH 8.0) containing 50 mM EDTA, 5% Triton X-100, 2 mM dithiothreitol and 8% sucrose. Thereto was added lysozyme so as to give a final concentration of 0.1%. The cell suspension was sonicated, and centrifuged to give insoluble inclusion bodies. The inclusion bodies were dissolved with SDS and subjected to SDS-polyacrylamide gel electrophoresis to detect a band of molecular weight about 13,000.

z. Solubilization and renaturation of inclusion bodies containing human D1HC protein All the inclusion bodies obtained in the above-mentioned y were dissolved in 10 ml of 50 mM Tris-HCl buffer (pH 7.4) containing 6M guanidine hydrochloride and 2 mM EDTA, and centrifuged to give a supernatant. The supernatant was dialyzed against PBS to give a solution containing human D1HC protein. Thus prepared human D1HC protein in an amount ranging from 2.5–0 μg was mixed with $1\times10^7$ Jurkat cells which were washed with the PBS containing 5% BSA and 1% glucose, and contained in 50 μl of the same buffer. Thereafter there was observed effect on rosette formation by adding $1\times10^7$ sheep erythrocytes. Human D1HC protein dose-dependently inhibited the rosette formation of Jurkat cells with sheep erythrocytes. The results are shown in FIG. 3.

EXAMPLE 6

α. Immobilization of sheep or human D1HC protein onto carrier

In 0.1M glycine buffer (pH 8.2) containing 15 mM NaCl was dissolved sheep D1HC protein prepared in the above-mentioned r or human D1HC protein prepared in the above-mentioned z so as to give 100 μg/ml of final concentration thereof. Thus obtained solution was added in an amount of 100 μl per well to 96-wells microtiter plate made by Costar (catalog number 3590), and incubated at 37° C. for 1 hour to coat bottom of wells in plate with the protein. Then, the plate was treated with 1% solution of BSA. After washing the plate thereto were added 2×10⁵ Jurkat cells per well which were washed with the PBS containing 5% BSA and 1% glucose and suspended in 100 µl of the same buffer. The plate was allowed to stand for 30 minutes at 4° C. The plate was washed 3 times with PBS, then cells adhered to the bottom of wells were observed. As a result, it is found that the cells adhered over the bottom of wells coated with sheep D1HC protein or human D1HC protein. In contrast, the cells hardly adhered to the bottom of wells coated with no D1HC protein.

EXAMPLE 7

β. Preparation of an expression vector of sheep D1HC protein containing cysteine residue (hereinafter referred to as "sheep D1HCcys protein") in $E. coli$ In order to make cDNA of sheep D1HC protein having cysteine residue at carboxyl terminal express in $E. coli$, an expression vector was constructed. The DNA of plasmid pKSLD1HC having cDNA of sheep D1HC protain obtained in the above-mentioned p was used as a template to carry out PCR. Used 5' primer is the primer used in the above-mentioned p and shown in SEQ ID NO: 9. Used 3' primer is shown in SEQ ID NO: 24. The primer is comprised of HindIII recognition sequence, PstI recognition sequence, sequence of termination codon, sequence coding for cysteine residue and then the following 318th–295 th nucleotide sequence of SEQ ID NO: 21. PCR was carried out by using the primers of SEQ ID NO: 9 and SEQ ID NO: 24 to amplify DNA fragments. Thus amplified DNA fragments were cleaved with restriction enzymes BamHI and PstI. The cleaved fragment was inserted into BamHI-PstI site of M13mp19 phage vector to give a recombinant vector. Nucleotide sequence of DNA introduced in the recombinant vector was confirmed by dideoxy method. Then, cDNA coding for sheep D1HCcys protein was taken out from the M13mp19 phage vector by cleaving with restriction enzymes NcoI and PstI. Thus obtained DNA was connected to NcoI-PstI site of vector pKK233-2 (made by Pharmacia) to give an expression vector pKSLD1HCcys. SEQ ID NO: 25 shows the nucleotide sequence from initiation codon to termination codon coding for sheep D1HCcys protein contained in pKSLD1HCcys.

γ. Production of sheep D1HCcys protein by using $E. coli$ as host $E. coli$ JM 109 (made by TAKARA SHUZO Co. ) was precultured which has the expression vector pKSLD1HCcys of sheep D1HCcys protein. Then, the precultured $E. coli$ was inoculated in 100 ml of LB medium containing 10 mg of ampicilline, and shaking culture was carried out at 37° C. in 500 ml of Sakaguchi flask until $A_{600}$ of the medium containing $E. coli$ became 0.3. Successively thereto was added IPTG so as to give a final concentration of 1 mM and further culture was continued for 6 hours. The cultured cells were collected by centrifugation, and suspended in 10 ml of 50 mM Tris-HCl buffer (pH 8.0) containing 50 mM EDTA, 5% Triton X-100, 2ram dithiothreitol and 8% sucrose. Thereto was added lysozyme so as to give a final concentration of 0.1%. The cell suspension was sonicated, and centrifuged to give insoluble inclusion bodies. The obtained inclusion bodies were dissolved with SDS and subjected to SDS-polyacrylamide gel electrophoresis to detect a band of molecular weight about 13,000.

δ. Solubilization and renaturation of inclusion bodies containing sheep D1HCcys protein All the inclusion bodies obtained in the above-mentioned γ were dissolved in 10 ml of 50 mM Tris-HCl buffer (pH 7.4) containing 6M guanidine hydrochloride, 2 mM EDTA and 5mM 2-mercaptoethanol, and centrifuged to give a supernatant. The supernatant was dialyzed against PBS to give a solution containing sheep D1HCcys protein. Thus prepared sheep D1HCcys protein in an amount ranging from 2.5–0 µg was mixed with 1×10⁵ Jurkat cells which were washed with the PBS containing 5% BSA and 1% glucose, and contained in 50 µl of the same buffer. Thereafter there was observed effect on rosette formation by adding 1×10⁷ sheep erythrocytes. Sheep D1HCcys protein dose-dependently inhibited the rosette formation of Jurkat cells with sheep erythrocytes.

EXAMPLE 8

ε. Preparation of an expression vector of human D1HC protein containing cysteine residue (hereinafter referred to as "human D1HCcys protein") in $E. coli$ In order to make cDNA of human D1HC protein having cysteine residue at carboxyl terminal express in $E. coli$, an expression vector was constructed. The DNA of plasmid pKHLD1HC having cDNA of human D1HC protein obtained in the above-mentioned x, was used as a template to carry out PCR. Used 5' primer is the primer used in the above-mentioned x and shown in SEQ ID NO: 17. Used 3' primer is shown in SEQ ID NO: 26. The primer is comprised of HindIII recognition sequence, sequence of termination codon, sequence coding for cysteine residue and the DNA sequence designed according to the sequence of the 330th–310th amino acids of SEQ ID NO: 23. PCR was carried out by using the primers of SEQ ID NO: 17 and SEQ ID NO: 26 to amplify DNA fragments. Thus amplified DNA fragments were cleaved with restriction enzymes KpnI and HindIII. The cleaved fragments was connected to KpnI-HindIII site of vector pKK233Kpn to give the expression vector pKHLD1HCcys. SEQ ID No: 27 shows the nucleotide sequence from initiation codon to termination codon coding for human D1HCcys protein contained in pKHLD1HCcys.

ζ. Production of human D1HCcys protein by using $E. coli$ as host $E. coli$ JM 109 (made by TAKARA SHUZO Co.) was precultured which has the expression vector pKHLD1HCcys of human D1HCcys protein. Then, the precultured $E. coli$ was inoculated in 100 ml of LB medium containing 10 mg of ampicilline, and shaking culture was carried out at 37° C. in 500 ml of Sakaguchi flask until $A_{600}$ of the medium containing $E. coli$ became 0.3. Successively thereto was added IPTG so as to give a final concentration of 1 mM and further culture was continued for 6 hours. The cultured cells were collected by centrifugation, and suspended in 10 ml of 50 mM Tris-HCl buffer (pH 8.0) containing 50 mM EDTA, 5% Triton X-100, 2 mM dithiothreitol and 8% sucrose. Thereto was added lysozyme so as to give a final concentration of 0.1%. The cell suspension was sonicated, and centrifuged to give insoluble inclusion bodies. The obtained inclusion bodies were dissolved with SDS and subjected to SDS-polyacrylamide gel electrophoresis to detect a band of molecular weight about 13,000.

η. Solubilization and renaturation of inclusion bodies containing human D1HCcys protein All the inclusion bodies obtained in the above-mentioned C were dissolved in 10 ml of 50 mM Tris-HCl buffer (pH 7.4) containing 6M guanidine hydrochloride, 2 mM EDTA and 5 mM 2-mercaptoethanol, and centrifuged to give a supernatant. The supernatant was dialyzed against PBS to give a solution containing human D1HCcys protein. Thus prepared human D1HCcys protein in an amount ranging from 2.5–0 μg was mixed with 1×10$^5$ Jurkat cells washed with the PBS containing 5% BSA and 1% glucose, and contained in 50 μl of the same buffer. Thereafter there was observed effect on rosette formation by adding 1×10$^7$ sheep erythrocytes. Human D1HCcys protein dose-dependently inhibited the rosette formation of Jurkat cells with sheep erythrocytes.

EXAMPLE 9

θ. Cloning of cDNA coding for human LFA-3

There was carried out cloning of cDNA coding for a full-length protein of human LFA-3. In the same manner as in the above-mentioned t, poly(A)$^+$RNA from human T-cell line MOLT-4 was purified. Further the purified poly(A)$^+$ RNA was used to synthesize double strand cDNA.

From the double strand cDNA was amplified cDNA coding for human LFA-3 protein by using 2 kinds of primers synthesized in the above-mentioned s being shown in SEQ ID No: 14 and SEQ ID NO: 15 by PCR method in vitro under the same condition as in the above-mentioned u. After completing the reaction, size of PCR products was measured by a polyacrylamide gel electrophoresis, and then it was found that DNA fragments of about 800 base pairs were amplified. The DNA fragments of about 800 base pairs were extracted from the gel and treated with restriction enzyme PstI. Then, the treated DNA was inserted into PstI site of pUC19 vector (made by TAKARA SHUZO Co.) and cloned by using *E. coli* JM 109 as host.

Then, in order to sequence the DNA amplified by PCR, DNA fragment of about 800 base pairs cleaved with PstI was inserted into PstI site of M13mp19 phage vector (made by TAKARA SHUZO Co.) and determined by a conventional method using dideoxynucleotide triphosphates. As a result, cDNA sequence of human LFA-3 protein shown in SEQ ID NO: 16 was found among DNA fragments of about 800 base pairs. The amino acid sequence of human LFA-3 protein encoded by such cDNA sequence completely coincided with that of human LFA-3 (SEQ ID NO: 8) previously reported by B. P. Wallner et al. (Journal of Experimental Medicine, vol. 166, p 923, 1987).

ι. Preparation of an expression vector of soluble human D1 protein having a part of amino acid sequence of D2 region in *E. coli*

In order to make DNA coding for soluble human D1 protein having the sequence from N-terminus to the first cysteine residue of D2 region (hereinafter referred to as "human D1cys protein") express in *E. coli*, an expression vector was constructed. As a template was used cDNA of human LFA-3 protein obtained in the above-mentioned θ to carry out PCR. Used 5' primer is the primer used in the above-mentioned x and shown in SEQ ID NO: 17. Used 3' primer is shown in SEQ ID NO: 28. The primer is comprised of HindIII recognition sequence, sequence of termination codon, sequence coding for cysteine residue and the DNA sequence designed according to the sequence of the 102nd–96th amino acids of SEQ ID NO: 8. PCR was carried out by using the primers of SEQ ID NO: 17 and SEQ ID NO: 28 to amplify DNA fragments. Thus amplified DNA fragments were cleaved with restriction enzymes KpnI and HindIII.

The cleaved fragment was connected to KpnI-HindIII site of vector pKK233Kpn to give an expression vector pKHLD1cys. SEQ ID NO: 29 shows the nucleotide sequence from initiation codon to termination codon coding for human D1 cys protein contained in pKHLD1cys.

κ. Production of human D1 cys protein by using *E. coli* as host

*E. coli* JM 109 (made by TAKARA SHUZO Co.) was precultured which has the expression vector pKHLD1cys of human D1 cys protein. Then, the precultured *E. coli* was inoculated in 100 ml of LB medium containing 10 mg of ampicilline, and shaking culture was carried out at 37° C. in 500 ml of Sakaguchi flask until $A_{600}$ of the medium containing *E. coli* became 0.3. Successively thereto was added IPTG so as to give a final concentration of 1 mM and further culture was continued for 6 hours. The cultured cells were collected by centrifugation, and suspended in 10 ml of 50 mM Tris-HCl buffer (pH 8.0) containing 50 mM EDTA, 5% Triton X-100 and 8% sucrose. Thereto was added lysozyme so as to give a final concentration of 1%. The cell suspension was sonicated, and centrifuged to give an insoluble precipitation fraction. The obtained precipitation was washed with 50% glycerol and sucessively with ethanol to give inclusion bodies containing produced human D1cys protein. The inclusion bodies were dissolved with SDS and subjected to SDS-polyacrylamide gel electrophoresis to detect a band of molecular weight about 12,000.

λ. Solubilization and renaturation of inclusion bodies containing human D1 cys protein All the inclusion bodies obtained in the above-mentioned β were dissolved in 10 ml of 50 mM Tris-HCl buffer (pH 7.4) containing 6M guanidine hydrochloride, 2 mM EDTA, and 5 mM 2-mercaptoethanol, and centrifuged to give a supernatant. The supernatant was dialyzed against PBS to give a solution containing human D1cys protein.

In addition to the ingredients used in the Examples, other ingredients can be used in the Examples as set forth in the specification to obtain substantially the same results.

---

What we claim is:

1. A recombinant LFA-3 like protein consisting of the amino acid sequence of SEQ ID NO: 36.

2. A recombinant LFA-3 like protein consisting of the amino acid sequence of SEQ ID NO: 1.

3. A recombinant LFA-3 like protein consisting of the amino acid sequence of SEQ ID NO: 13.

4. A recombinant LFA-3 like protein consisting of the peptide encoded by the DNA sequence of SEQ ID NO: 21.

5. A recombinant LFA-3 like protein consisting of the peptide encoded by the DNA sequence of SEQ ID NO: 23.

6. A recombinant LFA-3 like protein consisting of the peptide encoded by the DNA sequence of SEQ ID NO: 25.

7. A recombinant LFA-3 like protein consisting of the peptide encoded by the DNA sequence of SEQ ID NO: 27.

8. A recombinant LFA-3 like protein consisting of the peptide encoded by the DNA sequence of SEQ ID NO: 29.

* * * * *

SEQUENCE LISTING ( 1 ) GENERAL INFORMATION:

( i i i ) NUMBER OF SEQUENCES: 38

( 2 ) INFORMATION FOR SEQ ID NO:1:

( i ) SEQUENCE CHARACTERISTICS:
        ( A ) LENGTH: 131 amino acids
        ( B ) TYPE: amino acid
        ( D ) TOPOLOGY: linear ( v i ) ORIGINAL SOURCE:

(A) ORGANISM: Ovis
(G) CELL TYPE: Leukocyte (xi) SEQUENCE DESCRIPTION: SEQ ID NO:1:

| Val | Ser | Gln | Asp | Ile | Tyr | Gly | Ala | Met | Asn | Gly | Asn | Val | Thr | Phe | Tyr |
|---|---|---|---|---|---|---|---|---|---|---|---|---|---|---|---|
| 1 | | | | 5 | | | | | 10 | | | | | 15 | |

| Val | Ser | Glu | Ser | Gln | Pro | Phe | Thr | Glu | Ile | Met | Trp | Lys | Lys | Gly | Lys |
|---|---|---|---|---|---|---|---|---|---|---|---|---|---|---|---|
| | | | 20 | | | | | 25 | | | | | 30 | | |

| Asp | Lys | Val | Val | Glu | Trp | Asp | Gln | Thr | Ser | Gly | Leu | Glu | Ala | Phe | Gln |
|---|---|---|---|---|---|---|---|---|---|---|---|---|---|---|---|
| | | 35 | | | | | 40 | | | | | 45 | | | |

| Ser | Phe | Lys | Asn | Arg | Val | His | Leu | Asp | Ile | Val | Ser | Gly | Asn | Leu | Thr |
|---|---|---|---|---|---|---|---|---|---|---|---|---|---|---|---|
| | 50 | | | | | 55 | | | | | 60 | | | | |

| Ile | Thr | Gly | Leu | Thr | Lys | Leu | Asp | Glu | Asp | Val | Tyr | Glu | Ile | Glu | Ser |
|---|---|---|---|---|---|---|---|---|---|---|---|---|---|---|---|
| 65 | | | | 70 | | | | | 75 | | | | | 80 | |

| Pro | Ser | Val | Lys | Lys | Ser | Ser | Gln | Phe | His | Leu | Arg | Val | Ile | Asp | Tyr |
|---|---|---|---|---|---|---|---|---|---|---|---|---|---|---|---|
| | | | | 85 | | | | | 90 | | | | | 95 | |

| Ala | Arg | His | Arg | Tyr | Val | Leu | Phe | Ala | Ile | Leu | Pro | Ala | Val | Ile | Cys |
|---|---|---|---|---|---|---|---|---|---|---|---|---|---|---|---|
| | | | 100 | | | | | 105 | | | | | 110 | | |

| Gly | Leu | Leu | Phe | Leu | Lys | Cys | Phe | Leu | Gly | Arg | Arg | Ser | Gln | Arg | Asn |
|---|---|---|---|---|---|---|---|---|---|---|---|---|---|---|---|
| | | 115 | | | | | 120 | | | | | 125 | | | |

| Ser | Gly | Pro |
|---|---|---|
| | | 130 |

(2) INFORMATION FOR SEQ ID NO:2:

(i) SEQUENCE CHARACTERISTICS:
(A) LENGTH: 393 base pairs
(B) TYPE: nucleic acid
(C) STRANDEDNESS: single
(D) TOPOLOGY: linear (ii) MOLECULE TYPE: cDNA to mRNA (iii) HYPOTHETICAL: NO (vi) ORIGINAL SOURCE:
(A) ORGANISM: Ovis
(G) CELL TYPE: Leukocyte (xi) SEQUENCE DESCRIPTION: SEQ ID NO:2:

| GTT | TCC | CAA | GAT | ATT | TAT | GGA | GCT | ATG | AAT | GGG | AAT | GTA | ACC | TTT | TAC | 48 |
|---|---|---|---|---|---|---|---|---|---|---|---|---|---|---|---|---|
| Val | Ser | Gln | Asp | Ile | Tyr | Gly | Ala | Met | Asn | Gly | Asn | Val | Thr | Phe | Tyr | |
| 1 | | | | 5 | | | | | 10 | | | | | 15 | | |

| GTT | TCA | GAG | TCT | CAA | CCG | TTT | ACA | GAG | ATT | ATG | TGG | AAG | AAG | GGG | AAG | 96 |
|---|---|---|---|---|---|---|---|---|---|---|---|---|---|---|---|---|
| Val | Ser | Glu | Ser | Gln | Pro | Phe | Thr | Glu | Ile | Met | Trp | Lys | Lys | Gly | Lys | |
| | | | 20 | | | | | 25 | | | | | 30 | | | |

| GAT | AAA | GTT | GTA | GAA | TGG | GAT | CAA | ACA | TCT | GGA | CTC | GAA | GCT | TTT | CAG | 144 |
|---|---|---|---|---|---|---|---|---|---|---|---|---|---|---|---|---|
| Asp | Lys | Val | Val | Glu | Trp | Asp | Gln | Thr | Ser | Gly | Leu | Glu | Ala | Phe | Gln | |
| | | 35 | | | | | 40 | | | | | 45 | | | | |

| TCT | TTT | AAA | AAT | AGA | GTT | CAT | TTA | GAC | ATT | GTG | TCA | GGT | AAC | CTC | ACC | 192 |
|---|---|---|---|---|---|---|---|---|---|---|---|---|---|---|---|---|
| Ser | Phe | Lys | Asn | Arg | Val | His | Leu | Asp | Ile | Val | Ser | Gly | Asn | Leu | Thr | |
| | 50 | | | | | 55 | | | | | 60 | | | | | |

| ATC | ACC | GGG | TTA | ACA | AAA | TTA | GAT | GAA | GAT | GTG | TAT | GAA | ATT | GAA | TCC | 240 |
|---|---|---|---|---|---|---|---|---|---|---|---|---|---|---|---|---|
| Ile | Thr | Gly | Leu | Thr | Lys | Leu | Asp | Glu | Asp | Val | Tyr | Glu | Ile | Glu | Ser | |
| 65 | | | | 70 | | | | | 75 | | | | | 80 | | |

| CCA | AGT | GTT | AAA | AAG | AGC | TCC | CAG | TTC | CAC | CTC | AGA | GTG | ATT | GAT | TAT | 288 |
|---|---|---|---|---|---|---|---|---|---|---|---|---|---|---|---|---|
| Pro | Ser | Val | Lys | Lys | Ser | Ser | Gln | Phe | His | Leu | Arg | Val | Ile | Asp | Tyr | |
| | | | | 85 | | | | | 90 | | | | | 95 | | |

| GCA | AGG | CAT | AGG | TAT | GTG | CTT | TTT | GCC | ATA | CTG | CCA | GCA | GTA | ATA | TGT | 336 |
|---|---|---|---|---|---|---|---|---|---|---|---|---|---|---|---|---|
| Ala | Arg | His | Arg | Tyr | Val | Leu | Phe | Ala | Ile | Leu | Pro | Ala | Val | Ile | Cys | |
| | | | 100 | | | | | 105 | | | | | 110 | | | |

| GGC | TTG | CTG | TTT | TTA | AAA | TGT | TTT | CTG | GGA | CGT | CGT | AGC | CAA | CGA | AAC | 384 |

```
Gly  Leu  Leu  Phe  Leu  Lys  Cys  Phe  Leu  Gly  Arg  Arg  Ser  Gln  Arg  Asn
          115                 120                      125
```

```
TCA  GGG  CCC                                                                              393
Ser  Gly  Pro
     130
```

( 2 ) INFORMATION FOR SEQ ID NO:3:

( i ) SEQUENCE CHARACTERISTICS:
        ( A ) LENGTH: 29 amino acids
        ( B ) TYPE: amino acid
        ( D ) TOPOLOGY: unknown ( i i ) MOLECULE TYPE: peptide ( i i i ) HYPOTHETICAL: YES ( v ) FRAGMENT TYPE: N-terminal ( i x ) FEATURE: "Xaa"at position 1 represents either Val or Phe.
        " Xaa"at position 3 represents either Gln or Ser.
        " Xaa"at positions 12 and 28 represent one of the
        natural amino acids, the one at position 12 being
        preferably Ser.

( x i ) SEQUENCE DESCRIPTION: SEQ ID NO:3:

```
Xaa  Ser  Xaa  Asp  Ile  Tyr  Gly  Ala  Met  Asn  Gly  Xaa  Val  Thr  Phe  Tyr
1                   5                        10                       15

Val  Ser  Glu  Ser  Gln  Pro  Phe  Thr  Glu  Ile  Met  Xaa  Lys
          20                       25
```

( 2 ) INFORMATION FOR SEQ ID NO:4:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: synthetic DNA ( i i i ) HYPOTHETICAL: NO ( x i ) SEQUENCE DESCRIPTION: SEQ ID NO:4:

```
GTTGGATCCT  TYWSNCARGA  YATHTAYGG                                                           29
```

( 2 ) INFORMATION FOR SEQ ID NO:5:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: synthetic DNA ( i i i ) HYPOTHETICAL: NO ( i v ) ANTI-SENSE: YES ( x i ) SEQUENCE DESCRIPTION: SEQ ID NO:5:

```
ACACTGCAGC  ATDATYTCNG  TRAANGG                                                             27
```

( 2 ) INFORMATION FOR SEQ ID NO:6:

( i ) SEQUENCE CHARACTERISTICS:
        ( A ) LENGTH: 24 base pairs
        ( B ) TYPE: nucleic acid
        ( C ) STRANDEDNESS: single (D) TOPOLOGY: linear (ii) MOLECULE TYPE: other nucleic acid
(A) DESCRIPTION: synthetic DNA (iii) HYPOTHETICAL: NO (xi) SEQUENCE DESCRIPTION: SEQ ID NO:6:

AGCTATGAAC GGGAATGTAA CCTT    24

(2) INFORMATION FOR SEQ ID NO:7:

(i) SEQUENCE CHARACTERISTICS:
(A) LENGTH: 24 base pairs
(B) TYPE: nucleic acid
(C) STRANDEDNESS: single
(D) TOPOLOGY: linear (ii) MOLECULE TYPE: other nucleic acid
(A) DESCRIPTION: synthetic DNA (iii) HYPOTHETICAL: NO (xi) SEQUENCE DESCRIPTION: SEQ ID NO:7:

ACCTTTTACG TTTCAGAGTC TCAA    24

(2) INFORMATION FOR SEQ ID NO:8:

(i) SEQUENCE CHARACTERISTICS:
(A) LENGTH: 222 amino acids
(B) TYPE: amino acid
(D) TOPOLOGY: linear (iii) HYPOTHETICAL: NO (vi) ORIGINAL SOURCE:
(A) ORGANISM: Homo sapiens
(G) CELL TYPE: peripheral blood lymphocytes (x) PUBLICATION INFORMATION:
(A) AUTHORS: Wallner, Barbara P.
Frey, Alexis Z.
(B) TITLE: Primary Structure of Lymphocyte
Function- Associated Antigen 3 (LFA-3)
(C) JOURNAL: J. Exp. Med.
(D) VOLUME: 166
(F) PAGES: 923-932
(G) DATE: OCT-1987

(xi) SEQUENCE DESCRIPTION: SEQ ID NO:8:

```
Phe Ser Gln Gln Ile Tyr Gly Val Val Tyr Gly Asn Val Thr Phe His
1               5                   10                  15
Val Pro Ser Asn Val Pro Leu Lys Glu Val Leu Trp Lys Lys Gln Lys
                20                  25                  30
Asp Lys Val Ala Glu Leu Glu Asn Ser Glu Phe Arg Ala Phe Ser Ser
            35                  40                  45
Phe Lys Asn Arg Val Tyr Leu Asp Thr Val Ser Gly Ser Leu Thr Ile
        50                  55                  60
Tyr Asn Leu Thr Ser Ser Asp Glu Asp Glu Tyr Glu Met Glu Ser Pro
65                  70                  75                  80
Asn Ile Thr Asp Thr Met Lys Phe Phe Leu Tyr Val Leu Glu Ser Leu
                85                  90                  95
Pro Ser Pro Thr Leu Thr Cys Ala Leu Thr Asn Gly Ser Ile Glu Val
                100                 105                 110
Gln Cys Met Ile Pro Glu His Tyr Asn Ser His Arg Gly Leu Ile Met
            115                 120                 125
Tyr Ser Trp Asp Cys Pro Met Glu Gln Cys Lys Arg Asn Ser Thr Ser
```

```
          130                          135                          140
Ile Tyr Phe Lys Met Glu Asn Asp Leu Pro Gln Lys Ile Gln Cys Thr
145                 150                     155                 160
Leu Ser Asn Pro Leu Phe Asn Thr Thr Ser Ser Ile Ile Leu Thr Thr
                165                     170                 175
Cys Ile Pro Ser Ser Gly His Ser Arg His Arg Tyr Ala Leu Ile Pro
            180                 185                 190
Ile Pro Leu Ala Val Ile Thr Thr Cys Ile Val Leu Tyr Met Asn Gly
        195                 200             205
Ile Leu Lys Cys Asp Arg Lys Pro Asp Arg Thr Asn Ser Asn
    210                 215                 220
```

( 2 ) INFORMATION FOR SEQ ID NO:9:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: synthetic DNA ( i i i ) HYPOTHETICAL: NO ( x i ) SEQUENCE DESCRIPTION: SEQ ID NO:9:

TGGGGATCCA TGGTAAGTCA AGATATTTAT GG      32

( 2 ) INFORMATION FOR SEQ ID NO:10:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: synthetic DNA ( i i i ) HYPOTHETICAL: NO ( i v ) ANTI-SENSE: YES ( x i ) SEQUENCE DESCRIPTION: SEQ ID NO:10:

TTTGTCGACC TGCAGCTAGG GCCCTGAGTT TCGTTG      36

( 2 ) INFORMATION FOR SEQ ID NO:11:

( i ) SEQUENCE CHARACTERISTICS:
        ( A ) LENGTH: 51 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: synthetic DNA ( i i i ) HYPOTHETICAL: NO ( i v ) ANTI-SENSE: YES ( x i ) SEQUENCE DESCRIPTION: SEQ ID NO:11:

CAACTGCAGC TACGACGTCC CAGAAAACCT ATGCCTTGCA TAATCAATCA C      51

( 2 ) INFORMATION FOR SEQ ID NO:12:

( i ) SEQUENCE CHARACTERISTICS:
        ( A ) LENGTH: 402 base pairs (B) TYPE: nucleic acid
(C) STRANDEDNESS: both
(D) TOPOLOGY: linear (ii) MOLECULE TYPE: cDNA to mRNA (iii) HYPOTHETICAL: NO (vi) ORIGINAL SOURCE:
(A) ORGANISM: Homo sapiens
(H) CELL LINE: T cell line (vii) IMMEDIATE SOURCE:
(B) CLONE: MOLT-4

(xi) SEQUENCE DESCRIPTION: SEQ ID NO:12:

| TTT | TCC | CAA | CAA | ATA | TAT | GGT | GTT | GTG | TAT | GGG | AAT | GTA | ACT | TTC | CAT | 48 |
| Phe | Ser | Gln | Gln | Ile | Tyr | Gly | Val | Val | Tyr | Gly | Asn | Val | Thr | Phe | His | |
| 1 | | | | 5 | | | | | 10 | | | | | 15 | | |

| GTA | CCA | AGC | AAT | GTG | CCT | TTA | AAA | GAG | GTC | CTA | TGG | AAA | AAA | CAA | AAG | 96 |
| Val | Pro | Ser | Asn | Val | Pro | Leu | Lys | Glu | Val | Leu | Trp | Lys | Lys | Gln | Lys | |
| | | | 20 | | | | | 25 | | | | | 30 | | | |

| GAT | AAA | GTT | GCA | GAA | CTG | GAA | AAT | TCT | GAA | TTC | AGA | GCT | TTC | TCA | TCT | 144 |
| Asp | Lys | Val | Ala | Glu | Leu | Glu | Asn | Ser | Glu | Phe | Arg | Ala | Phe | Ser | Ser | |
| | | 35 | | | | | 40 | | | | | 45 | | | | |

| TTT | AAA | AAT | AGG | GTT | TAT | TTA | GAC | ACT | GTG | TCA | GGT | AGC | CTC | ACT | ATC | 192 |
| Phe | Lys | Asn | Arg | Val | Tyr | Leu | Asp | Thr | Val | Ser | Gly | Ser | Leu | Thr | Ile | |
| | 50 | | | | | 55 | | | | | 60 | | | | | |

| TAC | AAC | TTA | ACA | TCA | TCA | GAT | GAA | GAT | GAG | TAT | GAA | ATG | GAA | TCG | CCA | 240 |
| Tyr | Asn | Leu | Thr | Ser | Ser | Asp | Glu | Asp | Glu | Tyr | Glu | Met | Glu | Ser | Pro | |
| 65 | | | | | 70 | | | | | 75 | | | | | 80 | |

| AAT | ATT | ACT | GAT | ACC | ATG | AAG | TTC | TTT | CTT | TAT | GTG | CTT | GGT | CAT | TCA | 288 |
| Asn | Ile | Thr | Asp | Thr | Met | Lys | Phe | Phe | Leu | Tyr | Val | Leu | Gly | His | Ser | |
| | | | | 85 | | | | | 90 | | | | | 95 | | |

| AGA | CAC | AGA | TAT | GCA | CTT | ATA | CCC | ATA | CCA | TTA | GCA | GTA | ATT | ACA | ACA | 336 |
| Arg | His | Arg | Tyr | Ala | Leu | Ile | Pro | Ile | Pro | Leu | Ala | Val | Ile | Thr | Thr | |
| | | | 100 | | | | | 105 | | | | | 110 | | | |

| TGT | ATT | GTG | CTG | TAT | ATG | AAT | GGT | ATT | CTG | AAA | TGT | GAC | AGA | AAA | CCA | 384 |
| Cys | Ile | Val | Leu | Tyr | Met | Asn | Gly | Ile | Leu | Lys | Cys | Asp | Arg | Lys | Pro | |
| | | | 115 | | | | | 120 | | | | | 125 | | | |

| GAC | AGA | ACC | AAC | TCC | AAT | | | | | | | | | | | 402 |
| Asp | Arg | Thr | Asn | Ser | Asn | | | | | | | | | | | |
| | 130 | | | | | | | | | | | | | | | |

(2) INFORMATION FOR SEQ ID NO:13:

(i) SEQUENCE CHARACTERISTICS:
(A) LENGTH: 134 amino acids
(B) TYPE: amino acid
(D) TOPOLOGY: linear (ii) MOLECULE TYPE: protein (iii) HYPOTHETICAL: YES (xi) SEQUENCE DESCRIPTION: SEQ ID NO:13:

| Phe | Ser | Gln | Gln | Ile | Tyr | Gly | Val | Val | Tyr | Gly | Asn | Val | Thr | Phe | His |
| 1 | | | | 5 | | | | | 10 | | | | | 15 | |

| Val | Pro | Ser | Asn | Val | Pro | Leu | Lys | Glu | Val | Leu | Trp | Lys | Lys | Gln | Lys |
| | | | 20 | | | | | 25 | | | | | 30 | | |

| Asp | Lys | Val | Ala | Glu | Leu | Glu | Asn | Ser | Glu | Phe | Arg | Ala | Phe | Ser | Ser |
| | | 35 | | | | | 40 | | | | | 45 | | | |

| Phe | Lys | Asn | Arg | Val | Tyr | Leu | Asp | Thr | Val | Ser | Gly | Ser | Leu | Thr | Ile |
| | 50 | | | | | 55 | | | | | 60 | | | | |

| Tyr | Asn | Leu | Thr | Ser | Ser | Asp | Glu | Asp | Glu | Tyr | Glu | Met | Glu | Ser | Pro |

|     |     |     |     | 65  |     |     |     |     | 70  |     |     |     |     | 75  |     |     |     |     | 80  |
| --- | --- | --- | --- | --- | --- | --- | --- | --- | --- | --- | --- | --- | --- | --- | --- | --- | --- | --- | --- |
| Asn | Ile | Thr | Asp | Thr<br>85 | Met | Lys | Phe | Phe | Leu<br>90 | Tyr | Val | Leu | Gly | His<br>95 | Ser |
| Arg | His | Arg | Tyr<br>100 | Ala | Leu | Ile | Pro | Ile<br>105 | Pro | Leu | Ala | Val | Ile<br>110 | Thr | Thr |
| Cys | Ile | Val<br>115 | Leu | Tyr | Met | Asn | Gly<br>120 | Ile | Leu | Lys | Cys | Asp<br>125 | Arg | Lys | Pro |
| Asp | Arg<br>130 | Thr | Asn | Ser | Asn |

( 2 ) INFORMATION FOR SEQ ID NO:14:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: synthetic DNA ( i i i ) HYPOTHETICAL: NO ( x i ) SEQUENCE DESCRIPTION: SEQ ID NO:14:

CATCACCTGC AGCCATGGAT GGTTGCTGGG AGCGACGCGG GG      42

( 2 ) INFORMATION FOR SEQ ID NO:15:

( i ) SEQUENCE CHARACTERISTICS:
        ( A ) LENGTH: 41 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: synthetic DNA ( i i i ) HYPOTHETICAL: NO ( i v ) ANTI-SENSE: YES ( x i ) SEQUENCE DESCRIPTION: SEQ ID NO:15:

TTCACACTGC AGAATTCTCA ATTGGAGTTG GTTCTGTCTG G      41

( 2 ) INFORMATION FOR SEQ ID NO:16:

( i ) SEQUENCE CHARACTERISTICS:
        ( A ) LENGTH: 753 base pairs
        ( B ) TYPE: nucleic acid
        ( C ) STRANDEDNESS: both
        ( D ) TOPOLOGY: linear ( i i ) MOLECULE TYPE: cDNA to mRNA ( i i i ) HYPOTHETICAL: NO ( v i ) ORIGINAL SOURCE:
        ( A ) ORGANISM: Homo sapiens ( x ) PUBLICATION INFORMATION:
        ( A ) AUTHORS: Wallner, Barbara P
                 Frey, Alexis Z
        ( B ) TITLE: Primary Structure of Lymphocyte
                 Function- Associated Antigen 3 (LFA-3)
        ( C ) JOURNAL: J. Exp. Med.
        ( D ) VOLUME: 166
        ( F ) PAGES: 923-932
        ( G ) DATE: OCT-1987

( x i ) SEQUENCE DESCRIPTION: SEQ ID NO:16:

| | | | | | | | | | | | | | | | | |
|---|---|---|---|---|---|---|---|---|---|---|---|---|---|---|---|---|
| ATG | GTT | GCT | GGG | AGC | GAC | GCG | GGG | CGG | GCC | CTG | GGG | GTC | CTC | AGC | GTG | 48 |
| Met | Val | Ala | Gly | Ser | Asp | Ala | Gly | Arg | Ala | Leu | Gly | Val | Leu | Ser | Val | |
| -28 | | | -25 | | | | | -20 | | | | | -15 | | | |
| GTC | TGC | CTG | CTG | CAC | TGC | TTT | GGT | TTC | ATC | AGC | TGT | TTT | TCC | CAA | CAA | 96 |
| Val | Cys | Leu | Leu | His | Cys | Phe | Gly | Phe | Ile | Ser | Cys | Phe | Ser | Gln | Gln | |
| | | -10 | | | | | -5 | | | | | | 1 | | | |
| ATA | TAT | GGT | GTT | GTG | TAT | GGG | AAT | GTA | ACT | TTC | CAT | GTA | CCA | AGC | AAT | 144 |
| Ile | Tyr | Gly | Val | Val | Tyr | Gly | Asn | Val | Thr | Phe | His | Val | Pro | Ser | Asn | |
| 5 | | | | | 10 | | | | | 15 | | | | | 20 | |
| GTG | CCT | TTA | AAA | GAG | GTC | CTA | TGG | AAA | AAA | CAA | AAG | GAT | AAA | GTT | GCA | 192 |
| Val | Pro | Leu | Lys | Glu | Val | Leu | Trp | Lys | Lys | Gln | Lys | Asp | Lys | Val | Ala | |
| | | | | 25 | | | | | 30 | | | | | 35 | | |
| GAA | CTG | GAA | AAT | TCT | GAA | TTC | AGA | GCT | TTC | TCA | TCT | TTT | AAA | AAT | AGG | 240 |
| Glu | Leu | Glu | Asn | Ser | Glu | Phe | Arg | Ala | Phe | Ser | Ser | Phe | Lys | Asn | Arg | |
| | | | 40 | | | | | 45 | | | | | 50 | | | |
| GTT | TAT | TTA | GAC | ACT | GTG | TCA | GGT | AGC | CTC | ACT | ATC | TAC | AAC | TTA | ACA | 288 |
| Val | Tyr | Leu | Asp | Thr | Val | Ser | Gly | Ser | Leu | Thr | Ile | Tyr | Asn | Leu | Thr | |
| | | 55 | | | | | 60 | | | | | 65 | | | | |
| TCA | TCA | GAT | GAA | GAT | GAG | TAT | GAA | ATG | GAA | TCG | CCA | AAT | ATT | ACT | GAT | 336 |
| Ser | Ser | Asp | Glu | Asp | Glu | Tyr | Glu | Met | Glu | Ser | Pro | Asn | Ile | Thr | Asp | |
| | 70 | | | | | 75 | | | | | 80 | | | | | |
| ACC | ATG | AAG | TTC | TTT | CTT | TAT | GTG | CTT | GAG | TCT | CTT | CCA | TCT | CCC | ACA | 384 |
| Thr | Met | Lys | Phe | Phe | Leu | Tyr | Val | Leu | Glu | Ser | Leu | Pro | Ser | Pro | Thr | |
| 85 | | | | | 90 | | | | | 95 | | | | | 100 | |
| CTA | ACT | TGT | GCA | TTG | ACT | AAT | GGA | AGC | ATT | GAA | GTC | CAA | TGC | ATG | ATA | 432 |
| Leu | Thr | Cys | Ala | Leu | Thr | Asn | Gly | Ser | Ile | Glu | Val | Gln | Cys | Met | Ile | |
| | | | | 105 | | | | | 110 | | | | | 115 | | |
| CCA | GAG | CAT | TAC | AAC | AGC | CAT | CGA | GGA | CTT | ATA | ATG | TAC | TCA | TGG | GAT | 480 |
| Pro | Glu | His | Tyr | Asn | Ser | His | Arg | Gly | Leu | Ile | Met | Tyr | Ser | Trp | Asp | |
| | | | 120 | | | | | 125 | | | | | 130 | | | |
| TGT | CCT | ATG | GAG | CAA | TGT | AAA | CGT | AAC | TCA | ACC | AGT | ATA | TAT | TTT | AAG | 528 |
| Cys | Pro | Met | Glu | Gln | Cys | Lys | Arg | Asn | Ser | Thr | Ser | Ile | Tyr | Phe | Lys | |
| | | 135 | | | | | 140 | | | | | 145 | | | | |
| ATG | GAA | AAT | GAT | CTT | CCA | CAA | AAA | ATA | CAG | TGT | ACT | CTT | AGC | AAT | CCA | 576 |
| Met | Glu | Asn | Asp | Leu | Pro | Gln | Lys | Ile | Gln | Cys | Thr | Leu | Ser | Asn | Pro | |
| | 150 | | | | | 155 | | | | | 160 | | | | | |
| TTA | TTT | AAT | ACA | ACA | TCA | TCA | ATC | ATT | TTG | ACA | ACC | TGT | ATC | CCA | AGC | 624 |
| Leu | Phe | Asn | Thr | Thr | Ser | Ser | Ile | Ile | Leu | Thr | Thr | Cys | Ile | Pro | Ser | |
| 165 | | | | | 170 | | | | | 175 | | | | | 180 | |
| AGC | GGT | CAT | TCA | AGA | CAC | AGA | TAT | GCA | CTT | ATA | CCC | ATA | CCA | TTA | GCA | 672 |
| Ser | Gly | His | Ser | Arg | His | Arg | Tyr | Ala | Leu | Ile | Pro | Ile | Pro | Leu | Ala | |
| | | | | 185 | | | | | 190 | | | | | 195 | | |
| GTA | ATT | ACA | ACA | TGT | ATT | GTG | CTG | TAT | ATG | AAT | GGT | ATT | CTG | AAA | TGT | 720 |
| Val | Ile | Thr | Thr | Cys | Ile | Val | Leu | Tyr | Met | Asn | Gly | Ile | Leu | Lys | Cys | |
| | | | 200 | | | | | 205 | | | | | 210 | | | |
| GAC | AGA | AAA | CCA | GAC | AGA | ACC | AAC | TCC | AAT | TGA | | | | | | 753 |
| Asp | Arg | Lys | Pro | Asp | Arg | Thr | Asn | Ser | Asn | | | | | | | |
| | | 215 | | | | | 220 | | | | | | | | | |

( 2 ) INFORMATION FOR SEQ ID NO:17:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: synthetic DNA ( i i i ) HYPOTHETICAL: NO ( x i ) SEQUENCE DESCRIPTION: SEQ ID NO:17:

TTTGGTACCG GATGTTTTCC CAACAAATAT ATGGTGTT                                    38

( 2 ) INFORMATION FOR SEQ ID NO:18:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: synthetic DNA ( i i i ) HYPOTHETICAL: NO ( i v ) ANTI-SENSE: YES ( x i ) SEQUENCE DESCRIPTION: SEQ ID NO:18:

TTTAAGCTTG CTAGCTCAAT TGGAGTTGGT TCTGTCTGGT TT                                42

( 2 ) INFORMATION FOR SEQ ID NO:19:

( i ) SEQUENCE CHARACTERISTICS:
        ( A ) LENGTH: 72 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: synthetic DNA ( i i i ) HYPOTHETICAL: NO ( i v ) ANTI-SENSE: YES ( x i ) SEQUENCE DESCRIPTION: SEQ ID NO:19:

ATCAAGCTTT CAATTGGAGT TGGTTCTGTC TGGTTTTCTG TCTCTGTGTC TTGAATGACC            60

AAGCACATAA AG                                                                72

( 2 ) INFORMATION FOR SEQ ID NO:20:

( i ) SEQUENCE CHARACTERISTICS:
        ( A ) LENGTH: 399 base pairs
        ( B ) TYPE: nucleic acid
        ( C ) STRANDEDNESS: single
        ( D ) TOPOLOGY: linear ( i i ) MOLECULE TYPE: cDNA to mRNA ( i i i ) HYPOTHETICAL: NO ( v i ) ORIGINAL SOURCE:
        ( A ) ORGANISM: OVIS
        ( G ) CELL TYPE: Leukocyte ( x i ) SEQUENCE DESCRIPTION: SEQ ID NO:20:

```
ATG GTA AGT CAA GAT ATT TAT GGA GCT ATG AAT GGG AAT GTA ACC TTT             48
Met Val Ser Gln Asp Ile Tyr Gly Ala Met Asn Gly Asn Val Thr Phe
 1               5                  10                  15

TAC GTT TCA GAG TCT CAA CCG TTT ACA GAG ATT ATG TGG AAG AAG GGG             96
Tyr Val Ser Glu Ser Gln Pro Phe Thr Glu Ile Met Trp Lys Lys Gly
             20                  25                  30

AAG GAT AAA GTT GTA GAA TGG GAT CAA ACA TCT GGA CTC GAA GCT TTT            144
Lys Asp Lys Val Val Glu Trp Asp Gln Thr Ser Gly Leu Glu Ala Phe
         35                  40                  45

CAG TCT TTT AAA AAT AGA GTT CAT TTA GAC ATT GTG TCA GGT AAC CTC            192
Gln Ser Phe Lys Asn Arg Val His Leu Asp Ile Val Ser Gly Asn Leu
     50                  55                  60

ACC ATC ACC GGG TTA ACA AAA TTA GAT GAA GAT GTG TAT GAA ATT GAA            240
```

| Thr | Ile | Thr | Gly | Leu | Thr | Lys | Leu | Asp | Glu | Asp | Val | Tyr | Glu | Ile | Glu |
| 65 | | | | | 70 | | | | 75 | | | | | | 80 |

| TCC | CCA | AGT | GTT | AAA | AAG | AGC | TCC | CAG | TTC | CAC | CTC | AGA | GTG | ATT | GAT | 288 |
| Ser | Pro | Ser | Val | Lys | Lys | Ser | Ser | Gln | Phe | His | Leu | Arg | Val | Ile | Asp | |
| | | | | 85 | | | | | 90 | | | | | 95 | | |

| TAT | GCA | AGG | CAT | AGG | TAT | GTG | CTT | TTT | GCC | ATA | CTG | CCA | GCA | GTA | ATA | 336 |
| Tyr | Ala | Arg | His | Arg | Tyr | Val | Leu | Phe | Ala | Ile | Leu | Pro | Ala | Val | Ile | |
| | | | 100 | | | | | 105 | | | | | 110 | | | |

| TGT | GGC | TTG | CTG | TTT | TTA | AAA | TGT | TTT | CTG | GGA | CGT | CGT | AGC | CAA | CGA | 384 |
| Cys | Gly | Leu | Leu | Phe | Leu | Lys | Cys | Phe | Leu | Gly | Arg | Arg | Ser | Gln | Arg | |
| | | | 115 | | | | | 120 | | | | | 125 | | | |

| AAC | TCA | GGG | CCC | TAG | | | | | | | | | | | | 399 |
| Asn | Ser | Gly | Pro | | | | | | | | | | | | | |
| | | | 130 | | | | | | | | | | | | | |

( 2 ) INFORMATION FOR SEQ ID NO:21:

( i ) SEQUENCE CHARACTERISTICS:
        ( A ) LENGTH: 321 base pairs
        ( B ) TYPE: nucleic acid
        ( C ) STRANDEDNESS: single
        ( D ) TOPOLOGY: linear ( i i i ) HYPOTHETICAL: NO ( x i ) SEQUENCE DESCRIPTION: SEQ ID NO:21:

| ATG | GTA | AGT | CAA | GAT | ATT | TAT | GGA | GCT | ATG | AAT | GGG | AAT | GTA | ACC | TTT | 48 |
| Met | Val | Ser | Gln | Asp | Ile | Tyr | Gly | Ala | Met | Asn | Gly | Asn | Val | Thr | Phe | |
| 1 | | | | 5 | | | | | 10 | | | | | 15 | | |

| TAC | GTT | TCA | GAG | TCT | CAA | CCG | TTT | ACA | GAG | ATT | ATG | TGG | AAG | AAG | GGG | 96 |
| Tyr | Val | Ser | Glu | Ser | Gln | Pro | Phe | Thr | Glu | Ile | Met | Trp | Lys | Lys | Gly | |
| | | | 20 | | | | | 25 | | | | | 30 | | | |

| AAG | GAT | AAA | GTT | GTA | GAA | TGG | GAT | CAA | ACA | TCT | GGA | CTC | GAA | GCT | TTT | 144 |
| Lys | Asp | Lys | Val | Val | Glu | Trp | Asp | Gln | Thr | Ser | Gly | Leu | Glu | Ala | Phe | |
| | | | 35 | | | | | 40 | | | | | 45 | | | |

| CAG | TCT | TTT | AAA | AAT | AGA | GTT | CAT | TTA | GAC | ATT | GTG | TCA | GGT | AAC | CTC | 192 |
| Gln | Ser | Phe | Lys | Asn | Arg | Val | His | Leu | Asp | Ile | Val | Ser | Gly | Asn | Leu | |
| | | | 50 | | | | | 55 | | | | | 60 | | | |

| ACC | ATC | ACC | GGG | TTA | ACA | AAA | TTA | GAT | GAA | GAT | GTG | TAT | GAA | ATT | GAA | 240 |
| Thr | Ile | Thr | Gly | Leu | Thr | Lys | Leu | Asp | Glu | Asp | Val | Tyr | Glu | Ile | Glu | |
| 65 | | | | | 70 | | | | 75 | | | | | | 80 | |

| TCC | CCA | AGT | GTT | AAA | AAG | AGC | TCC | CAG | TTC | CAC | CTC | AGA | GTG | ATT | GAT | 288 |
| Ser | Pro | Ser | Val | Lys | Lys | Ser | Ser | Gln | Phe | His | Leu | Arg | Val | Ile | Asp | |
| | | | | 85 | | | | | 90 | | | | | 95 | | |

| TAT | GCA | AGG | CAT | AGG | TTT | TCT | GGG | ACG | TCG | TAG | | | | | | 321 |
| Tyr | Ala | Arg | His | Arg | Phe | Ser | Gly | Thr | Ser | | | | | | | |
| | | | 100 | | | | | 105 | | | | | | | | |

( 2 ) INFORMATION FOR SEQ ID NO:22:

( i ) SEQUENCE CHARACTERISTICS:
        ( A ) LENGTH: 408 base pairs
        ( B ) TYPE: nucleic acid
        ( C ) STRANDEDNESS: both
        ( D ) TOPOLOGY: linear ( i i ) MOLECULE TYPE: cDNA to mRNA ( i i i ) HYPOTHETICAL: NO ( v i ) ORIGINAL SOURCE:
        ( A ) ORGANISM: Homo sapiens
        ( G ) CELL TYPE: T cell line ( v i i ) IMMEDIATE SOURCE:
        ( B ) CLONE: MOLT-4

( x i ) SEQUENCE DESCRIPTION: SEQ ID NO:22:

```
ATG TTT TCC CAA CAA ATA TAT GGT GTT GTG TAT GGG AAT GTA ACT TTC    48
Met Phe Ser Gln Gln Ile Tyr Gly Val Val Tyr Gly Asn Val Thr Phe
1               5                   10                  15

CAT GTA CCA AGC AAT GTG CCT TTA AAA GAG GTC CTA TGG AAA AAA CAA    96
His Val Pro Ser Asn Val Pro Leu Lys Glu Val Leu Trp Lys Lys Gln
            20                  25                  30

AAG GAT AAA GTT GCA GAA CTG GAA AAT TCT GAA TTC AGA GCT TTC TCA   144
Lys Asp Lys Val Ala Glu Leu Glu Asn Ser Glu Phe Arg Ala Phe Ser
        35                  40                  45

TCT TTT AAA AAT AGG GTT TAT TTA GAC ACT GTG TCA GGT AGC CTC ACT   192
Ser Phe Lys Asn Arg Val Tyr Leu Asp Thr Val Ser Gly Ser Leu Thr
    50                  55                  60

ATC TAC AAC TTA ACA TCA TCA GAT GAA GAT GAG TAT GAA ATG GAA TCG   240
Ile Tyr Asn Leu Thr Ser Ser Asp Glu Asp Glu Tyr Glu Met Glu Ser
65                  70                  75                  80

CCA AAT ATT ACT GAT ACC ATG AAG TTC TTT CTT TAT GTG CTT GGT CAT   288
Pro Asn Ile Thr Asp Thr Met Lys Phe Phe Leu Tyr Val Leu Gly His
                85                  90                  95

TCA AGA CAC AGA TAT GCA CTT ATA CCC ATA CCA TTA GCA GTA ATT ACA   336
Ser Arg His Arg Tyr Ala Leu Ile Pro Ile Pro Leu Ala Val Ile Thr
            100                 105                 110

ACA TGT ATT GTG CTG TAT ATG AAT GGT ATT CTG AAA TGT GAC AGA AAA   384
Thr Cys Ile Val Leu Tyr Met Asn Gly Ile Leu Lys Cys Asp Arg Lys
        115                 120                 125

CCA GAC AGA ACC AAC TCC AAT TGA                                   408
Pro Asp Arg Thr Asn Ser Asn
130                 135
```

( 2 ) INFORMATION FOR SEQ ID NO:23:

( i ) SEQUENCE CHARACTERISTICS:
        ( A ) LENGTH: 333 base pairs
        ( B ) TYPE: nucleic acid
        ( C ) STRANDEDNESS: both
        ( D ) TOPOLOGY: linear ( i i i ) HYPOTHETICAL: NO ( x i ) SEQUENCE DESCRIPTION: SEQ ID NO:23:

```
ATG TTT TCC CAA CAA ATA TAT GGT GTT GTG TAT GGG AAT GTA ACT TTC    48
Met Phe Ser Gln Gln Ile Tyr Gly Val Val Tyr Gly Asn Val Thr Phe
1               5                   10                  15

CAT GTA CCA AGC AAT GTG CCT TTA AAA GAG GTC CTA TGG AAA AAA CAA    96
His Val Pro Ser Asn Val Pro Leu Lys Glu Val Leu Trp Lys Lys Gln
            20                  25                  30

AAG GAT AAA GTT GCA GAA CTG GAA AAT TCT GAA TTC AGA GCT TTC TCA   144
Lys Asp Lys Val Ala Glu Leu Glu Asn Ser Glu Phe Arg Ala Phe Ser
        35                  40                  45

TCT TTT AAA AAT AGG GTT TAT TTA GAC ACT GTG TCA GGT AGC CTC ACT   192
Ser Phe Lys Asn Arg Val Tyr Leu Asp Thr Val Ser Gly Ser Leu Thr
    50                  55                  60

ATC TAC AAC TTA ACA TCA TCA GAT GAA GAT GAG TAT GAA ATG GAA TCG   240
Ile Tyr Asn Leu Thr Ser Ser Asp Glu Asp Glu Tyr Glu Met Glu Ser
65                  70                  75                  80

CCA AAT ATT ACT GAT ACC ATG AAG TTC TTT CTT TAT GTG CTT GGT CAT   288
Pro Asn Ile Thr Asp Thr Met Lys Phe Phe Leu Tyr Val Leu Gly His
                85                  90                  95

TCA AGA CAC AGA GAC AGA AAA CCA GAC AGA ACC AAC TCC AAT TGA       333
Ser Arg His Arg Asp Arg Lys Pro Asp Arg Thr Asn Ser Asn
            100                 105                 110
```

( 2 ) INFORMATION FOR SEQ ID NO:24:

( i ) SEQUENCE CHARACTERISTICS:
        ( A ) LENGTH: 46 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: synthetic DNA ( i i i ) HYPOTHETICAL: NO ( i v ) ANTI-SENSE: YES ( x i ) SEQUENCE DESCRIPTION: SEQ ID NO:24:

```
TTTTTTCGAA CTGCAGCTAA CACGACGTCC CAGAAAACCT ATGCCT                    46
```

( 2 ) INFORMATION FOR SEQ ID NO:25:

( i ) SEQUENCE CHARACTERISTICS:
        ( A ) LENGTH: 324 base pairs
        ( B ) TYPE: nucleic acid
        ( C ) STRANDEDNESS: both
        ( D ) TOPOLOGY: linear ( i i i ) HYPOTHETICAL: NO ( x i ) SEQUENCE DESCRIPTION: SEQ ID NO:25:

```
ATG GTA AGT CAA GAT ATT TAT GGA GCT ATG AAT GGG AAT GTA ACC TTT       48
Met Val Ser Gln Asp Ile Tyr Gly Ala Met Asn Gly Asn Val Thr Phe
 1           5                  10                  15

TAC GTT TCA GAG TCT CAA CCG TTT ACA GAG ATT ATG TGG AAG AAG GGG       96
Tyr Val Ser Glu Ser Gln Pro Phe Thr Glu Ile Met Trp Lys Lys Gly
             20                  25                  30

AAG GAT AAA GTT GTA GAA TGG GAT CAA ACA TCT GGA CTC GAA GCT TTT      144
Lys Asp Lys Val Val Glu Trp Asp Gln Thr Ser Gly Leu Glu Ala Phe
         35                  40                  45

CAG TCT TTT AAA AAT AGA GTT CAT TTA GAC ATT GTG TCA GGT AAC CTC      192
Gln Ser Phe Lys Asn Arg Val His Leu Asp Ile Val Ser Gly Asn Leu
     50                  55                  60

ACC ATC ACC GGG TTA ACA AAA TTA GAT GAA GAT GTG TAT GAA ATT GAA      240
Thr Ile Thr Gly Leu Thr Lys Leu Asp Glu Asp Val Tyr Glu Ile Glu
 65                  70                  75                  80

TCC CCA AGT GTT AAA AAG AGC TCC GAG TTC CAC CTC AGA GTG ATT GAT      288
Ser Pro Ser Val Lys Lys Ser Ser Glu Phe His Leu Arg Val Ile Asp
             85                  90                  95

TAT GCA AGG CAT AGG TTT TCT GGG ACG TCG TGT TAG                      324
Tyr Ala Arg His Arg Phe Ser Gly Thr Ser Cys
            100                 105
```

( 2 ) INFORMATION FOR SEQ ID NO:26:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: synthetic DNA ( i i i ) HYPOTHETICAL: NO ( i v ) ANTI-SENSE: YES ( x i ) SEQUENCE DESCRIPTION: SEQ ID NO:26:

```
GGGGAAGCTT TCAACAATTG GAGTTGGTTC TGTCTGG                              37
```

( 2 ) INFORMATION FOR SEQ ID NO:27:

( i ) SEQUENCE CHARACTERISTICS:
        ( A ) LENGTH: 336 base pairs
        ( B ) TYPE: nucleic acid
        ( C ) STRANDEDNESS: both
        ( D ) TOPOLOGY: linear ( i i i ) HYPOTHETICAL: NO ( x i ) SEQUENCE DESCRIPTION: SEQ ID NO:27:

```
ATG TTT TCC CAA CAA ATA TAT GGT GTT GTG TAT GGG AAT GTA ACT TTC      48
Met Phe Ser Gln Gln Ile Tyr Gly Val Val Tyr Gly Asn Val Thr Phe
 1               5                  10                  15

CAT GTA CCA AGC AAT GTG CCT TTA AAA GAG GTC CTA TGG AAA AAA CAA      96
His Val Pro Ser Asn Val Pro Leu Lys Glu Val Leu Trp Lys Lys Gln
             20                  25                  30

AAG GAT AAA GTT GCA GAA CTG GAA AAT TCT GAA TTC AGA GCT TTC TCA     144
Lys Asp Lys Val Ala Glu Leu Glu Asn Ser Glu Phe Arg Ala Phe Ser
         35                  40                  45

TCT TTT AAA AAT AGG GTT TAT TTA GAC ACT GTG TCA GGT AGC CTC ACT     192
Ser Phe Lys Asn Arg Val Tyr Leu Asp Thr Val Ser Gly Ser Leu Thr
     50                  55                  60

ATC TAC AAC TTA ACA TCA TCA GAT GAA GAT GAG TAT GAA ATG GAA TCG     240
Ile Tyr Asn Leu Thr Ser Ser Asp Glu Asp Glu Tyr Glu Met Glu Ser
 65                  70                  75                  80

CCA AAT ATT ACT GAT ACC ATG AAG TTC TTT CTT TAT GTG CTT GGT CAT     288
Pro Asn Ile Thr Asp Thr Met Lys Phe Phe Leu Tyr Val Leu Gly His
                 85                  90                  95

TCA AGA CAC AGA GAC AGA AAA CCA GAC AGA ACC AAC TCC AAT TGT TGA     336
Ser Arg His Arg Asp Arg Lys Pro Asp Arg Thr Asn Ser Asn Cys
             100                 105                 110
```

( 2 ) INFORMATION FOR SEQ ID NO:28:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: other nucleic acid
        ( B ) DESCRIPTION: synthetic DNA ( i i i ) HYPOTHETICAL: NO ( i v ) ANTI-SENSE: YES ( x i ) SEQUENCE DESCRIPTION: SEQ ID NO:28:

TTTAAGCTTC AACAAGTTAG TGTGGGAGAT GGAAG        35

( 2 ) INFORMATION FOR SEQ ID NO:29:

( i ) SEQUENCE CHARACTERISTICS:
        ( A ) LENGTH: 315 base pairs
        ( B ) TYPE: nucleic acid
        ( C ) STRANDEDNESS: both
        ( D ) TOPOLOGY: linear ( i i i ) HYPOTHETICAL: NO ( x i ) SEQUENCE DESCRIPTION: SEQ ID NO:29:

```
ATG TTT TCC CAA CAA ATA TAT GGT GTT GTG TAT GGG AAT GTA ACT TTC      48
Met Phe Ser Gln Gln Ile Tyr Gly Val Val Tyr Gly Asn Val Thr Phe
 1               5                  10                  15

CAT GTA CCA AGC AAT GTG CCT TTA AAA GAG GTC CTA TGG AAA AAA CAA      96
His Val Pro Ser Asn Val Pro Leu Lys Glu Val Leu Trp Lys Lys Gln
```

|  |  |  |  |  |  |  |  |  |  |  |  |  |  |  |  |  |
|---|---|---|---|---|---|---|---|---|---|---|---|---|---|---|---|---|
|  |  |  | 20 |  |  |  |  | 25 |  |  |  |  | 30 |  |  |  |
| AAG | GAT | AAA | GTT | GCA | GAA | CTG | GAA | AAT | TCT | GAA | TTC | AGA | GCT | TTC | TCA | 144 |
| Lys | Asp | Lys 35 | Val | Ala | Glu | Leu | Glu 40 | Asn | Ser | Glu | Phe | Arg 45 | Ala | Phe | Ser |  |
| TCT | TTT | AAA | AAT | AGG | GTT | TAT | TTA | GAC | ACT | GTG | TCA | GGT | AGC | CTC | ACT | 192 |
| Ser | Phe 50 | Lys | Asn | Arg | Val | Tyr 55 | Leu | Asp | Thr | Val | Ser 60 | Gly | Ser | Leu | Thr |  |
| ATC | TAC | AAC | TTA | ACA | TCA | TCA | GAT | GAA | GAT | GAG | TAT | GAA | ATG | GAA | TCG | 240 |
| Ile 65 | Tyr | Asn | Leu | Thr | Ser 70 | Ser | Asp | Glu | Asp | Glu 75 | Tyr | Glu | Met | Glu | Ser 80 |  |
| CCA | AAT | ATT | ACT | GAT | ACC | ATG | AAG | TTC | TTT | CTT | TAT | GTG | CTT | GAG | TCT | 288 |
| Pro | Asn | Ile | Thr | Asp 85 | Thr | Met | Lys | Phe | Phe 90 | Leu | Tyr | Val | Leu | Glu 95 | Ser |  |
| CTT | CCA | TCT | CCC | ACA | CTA | ACT | TGT | TGA |  |  |  |  |  |  |  | 315 |
| Leu | Pro | Ser | Pro 100 | Thr | Leu | Thr | Cys |  |  |  |  |  |  |  |  |  |

( 2 ) INFORMATION FOR SEQ ID NO:30:

( i ) SEQUENCE CHARACTERISTICS:
    ( A ) LENGTH: 675 base pairs
    ( B ) TYPE: nucleic acid
    ( C ) STRANDEDNESS: single
    ( D ) TOPOLOGY: linear ( i i ) MOLECULE TYPE: cDNA to mRNA ( i i i ) HYPOTHETICAL: NO ( v i ) ORIGINAL SOURCE:
    ( A ) ORGANISM: OVIS
    ( G ) CELL TYPE: leukocyte ( x i ) SEQUENCE DESCRIPTION: SEQ ID NO:30:

|  |  |  |  |  |  |  |  |  |  |  |  |  |  |  |  |  |
|---|---|---|---|---|---|---|---|---|---|---|---|---|---|---|---|---|
| GTT | TCC | CAA | GAT | ATT | TAT | GGA | GCT | ATG | AAT | GGG | AAT | GTA | ACC | TTT | TAC | 48 |
| Val 1 | Ser | Gln | Asp | Ile 5 | Tyr | Gly | Ala | Met | Asn 10 | Gly | Asn | Val | Thr | Phe 15 | Tyr |  |
| GTT | TCA | GAG | TCT | CAA | CCG | TTT | ACA | GAG | ATT | ATG | TGG | AAG | AAG | GGG | AAG | 96 |
| Val | Ser | Glu | Ser 20 | Gln | Pro | Phe | Thr | Glu 25 | Ile | Met | Trp | Lys | Lys 30 | Gly | Lys |  |
| GAT | AAA | GTT | GTA | GAA | TGG | GAT | CAA | ACA | TCT | GGA | CTC | GAA | GCT | TTT | CAG | 144 |
| Asp | Lys | Val 35 | Val | Glu | Trp | Asp | Gln 40 | Thr | Ser | Gly | Leu | Glu 45 | Ala | Phe | Gln |  |
| TCT | TTT | AAA | AAT | AGA | GTT | CAT | TTA | GAC | ATT | GTG | TCA | GGT | AAC | CTC | ACC | 192 |
| Ser | Phe 50 | Lys | Asn | Arg | Val | His 55 | Leu | Asp | Ile | Val | Ser 60 | Gly | Asn | Leu | Thr |  |
| ATC | ACC | GGG | TTA | ACA | AAA | TTA | GAT | GAA | GAT | GTG | TAT | GAA | ATT | GAA | TCC | 240 |
| Ile 65 | Thr | Gly | Leu | Thr | Lys 70 | Leu | Asp | Glu | Asp | Val 75 | Tyr | Glu | Ile | Glu | Ser 80 |  |
| CCA | AGT | GTT | AAA | AAG | AGC | TCC | CAG | TTG | CAC | CTC | AGA | GTG | ATT | GAA | CCT | 288 |
| Pro | Ser | Val | Lys | Lys 85 | Ser | Ser | Gln | Leu | His 90 | Leu | Arg | Val | Ile | Glu 95 | Pro |  |
| CCT | CCA | ACA | CCG | TCA | GCA | TCT | TGC | TTC | TTG | ACT | GAG | GGT | GGA | AAC | CTT | 336 |
| Pro | Pro | Thr | Pro 100 | Ser | Ala | Ser | Cys | Phe 105 | Leu | Thr | Glu | Gly | Gly 110 | Asn | Leu |  |
| ACT | CTC | ACC | TGC | TCG | ATC | CCG | GAA | GGT | GAC | CCC | AAA | GAG | CTC | GAT | GAT | 384 |
| Thr | Leu | Thr 115 | Cys | Ser | Ile | Pro | Glu 120 | Gly | Asp | Pro | Lys | Glu 125 | Leu | Asp | Asp |  |
| AGT | GAC | CTA | ATA | CGG | TAT | TTG | TGG | GAA | TGT | CCG | CCA | ACA | ATA | CAG | TGT | 432 |
| Ser | Asp | Leu 130 | Ile | Arg | Tyr | Leu | Trp 135 | Glu | Cys | Pro | Pro | Thr 140 | Ile | Gln | Cys |  |
| CAC | CGT | GGC | TCG | ATT | TCA | TCT | GAA | GCC | TTT | GTC | TCA | GCG | GAA | AGT | GAT | 480 |
| His 145 | Arg | Gly | Ser | Ile | Ser 150 | Ser | Glu | Ala | Phe | Val 155 | Ser | Ala | Glu | Ser | Asp 160 |  |

```
CTT  TCA  CAG  AAT  GTT  CAG  TGT  ATC  GTT  AGC  AAT  CCA  TTG  TTC  AGA  ACA       528
Leu  Ser  Gln  Asn  Val  Gln  Cys  Ile  Val  Ser  Asn  Pro  Leu  Phe  Arg  Thr
               165                      170                          175

TCA  GCT  TCC  GTC  TCT  TTG  TCA  ACC  TGT  TTG  CCA  GAG  GAT  TAT  GCA  AGG       576
Ser  Ala  Ser  Val  Ser  Leu  Ser  Thr  Cys  Leu  Pro  Glu  Asp  Tyr  Ala  Arg
               180                      185                          190

CAT  AGG  TAT  GTG  CTT  TTT  GCC  ATA  CTG  CCA  GCA  GTA  ATA  TGT  GGC  TTG       624
His  Arg  Tyr  Val  Leu  Phe  Ala  Ile  Leu  Pro  Ala  Val  Ile  Cys  Gly  Leu
               195                      200                          205

CTG  TTT  TTA  AAA  TGT  TTT  CTG  GGA  CGT  CGT  AGC  CAA  CGA  AAC  TCA  GGG       672
Leu  Phe  Leu  Lys  Cys  Phe  Leu  Gly  Arg  Arg  Ser  Gln  Arg  Asn  Ser  Gly
     210                      215                      220

CCC                                                                                   675
Pro
225
```

( 2 ) INFORMATION FOR SEQ ID NO:31:

( i ) SEQUENCE CHARACTERISTICS:
        ( A ) LENGTH: 225 amino acids
        ( B ) TYPE: amino acid
        ( D ) TOPOLOGY: linear ( i i ) MOLECULE TYPE: peptide ( i i i ) HYPOTHETICAL: YES ( x i ) SEQUENCE DESCRIPTION: SEQ ID NO:31:

```
Val  Ser  Gln  Asp  Ile  Tyr  Gly  Ala  Met  Asn  Gly  Asn  Val  Thr  Phe  Tyr
 1              5                        10                           15

Val  Ser  Glu  Ser  Gln  Pro  Phe  Thr  Glu  Ile  Met  Trp  Lys  Lys  Gly  Lys
          20                       25                      30

Asp  Lys  Val  Val  Glu  Trp  Asp  Gln  Thr  Ser  Gly  Leu  Glu  Ala  Phe  Gln
          35                       40                      45

Ser  Phe  Lys  Asn  Arg  Val  His  Leu  Asp  Ile  Val  Ser  Gly  Asn  Leu  Thr
     50                       55                      60

Ile  Thr  Gly  Leu  Thr  Lys  Leu  Asp  Glu  Asp  Val  Tyr  Glu  Ile  Glu  Ser
 65                      70                       75                           80

Pro  Ser  Val  Lys  Lys  Ser  Ser  Gln  Phe  His  Leu  Arg  Val  Ile  Glu  Pro
                85                       90                      95

Pro  Pro  Thr  Pro  Ser  Ala  Ser  Cys  Phe  Leu  Thr  Glu  Gly  Gly  Asn  Ile
               100                      105                     110

Thr  Leu  Thr  Cys  Ser  Ile  Pro  Glu  Gly  Asp  Pro  Lys  Glu  Leu  Asp  Asp
          115                      120                     125

Ser  Asp  Leu  Ile  Arg  Tyr  Leu  Trp  Glu  Cys  Pro  Pro  Thr  Ile  Gln  Cys
     130                      135                     140

His  Arg  Gly  Ser  Ile  Ser  Ser  Glu  Ala  Phe  Val  Ser  Ala  Glu  Ser  Asp
145                      150                      155                          160

Leu  Ser  Gln  Asn  Val  Gln  Cys  Ile  Val  Ser  Asn  Pro  Leu  Phe  Arg  Thr
               165                      170                          175

Ser  Ala  Ser  Val  Ser  Leu  Ser  Thr  Cys  Leu  Pro  Glu  Asp  Tyr  Ala  Arg
               180                      185                          190

His  Arg  Tyr  Val  Leu  Phe  Ala  Ile  Leu  Pro  Ala  Val  Ile  Cys  Gly  Leu
               195                      200                          205

Leu  Phe  Leu  Lys  Cys  Phe  Leu  Gly  Arg  Arg  Ser  Gln  Arg  Asn  Ser  Gly
     210                      215                      220

Pro
225
```

5,556,943

53                                                                                          54
-continued ( 2 ) INFORMATION FOR SEQ ID NO:32:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: synthetic DNA ( i i i ) HYPOTHETICAL: NO ( x i ) SEQUENCE DESCRIPTION: SEQ ID NO:32:

TTGGGGATCC ATGGTTTCCC AAGATATTTA TGG                                                        33

( 2 ) INFORMATION FOR SEQ ID NO:33:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: synthetic DNA ( i i i ) HYPOTHETICAL: NO ( x i ) SEQUENCE DESCRIPTION: SEQ ID NO:33:

TTGGGGATCC ATGGTAAGTC AAGATATTTA TGG                                                        33

( 2 ) INFORMATION FOR SEQ ID NO:34:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: synthetic DNA ( i i i ) HYPOTHETICAL: NO ( x i ) SEQUENCE DESCRIPTION: SEQ ID NO:34:

GTCGACCTGC AGCTACGACG TCCCAGAAAA CCTATG                                                     36

( 2 ) INFORMATION FOR SEQ ID NO:35:

( i ) SEQUENCE CHARACTERISTICS:
        ( A ) LENGTH: 597 base pairs
        ( B ) TYPE: nucleic acid
        ( C ) STRANDEDNESS: single
        ( D ) TOPOLOGY: linear ( i i ) MOLECULE TYPE: cDNA to mRNA ( i i i ) HYPOTHETICAL: NO ( v i ) ORIGINAL SOURCE:
        ( A ) ORGANISM: OVIS
        ( G ) CELL TYPE: Leukocyte ( x i ) SEQUENCE DESCRIPTION: SEQ ID NO:35:

```
GTT  TCC  CAA  GAT  ATT  TAT  GGA  GCT  ATG  AAT  GGG  AAT  GTA  ACC  TTT  TAC        48
Val  Ser  Gln  Asp  Ile  Tyr  Gly  Ala  Met  Asn  Gly  Asn  Val  Thr  Phe  Tyr
 1                    5                        10                       15

GTT  TCA  GAG  TCT  CAA  CCG  TTT  ACA  GAG  ATT  ATG  TGG  AAG  AAG  GGG  AAG        96
Val  Ser  Glu  Ser  Gln  Pro  Phe  Thr  Glu  Ile  Met  Trp  Lys  Lys  Gly  Lys
              20                        25                       30
```

```
GAT  AAA  GTT  GTA  GAA  TGG  GAT  CAA  ACA  TCT  GGA  CTC  GAA  GCT  TTT  CAG       144
Asp  Lys  Val  Val  Glu  Trp  Asp  Gln  Thr  Ser  Gly  Leu  Glu  Ala  Phe  Gln
          35                       40                      45

TCT  TTT  AAA  AAT  AGA  GTT  CAT  TTA  GAC  ATT  GTG  TCA  GGT  AAC  CTC  ACC       192
Ser  Phe  Lys  Asn  Arg  Val  His  Leu  Asp  Ile  Val  Ser  Gly  Asn  Leu  Thr
     50                       55                      60

ATC  ACC  GGG  TTA  ACA  AAA  TTA  GAT  GAA  GAT  GTG  TAT  GAA  ATT  GAA  TCC       240
Ile  Thr  Gly  Leu  Thr  Lys  Leu  Asp  Glu  Asp  Val  Tyr  Glu  Ile  Glu  Ser
65                       70                      75                           80

CCA  AGT  GTT  AAA  AAG  AGC  TCC  CAG  TTC  CAC  CTC  AGA  GTG  ATT  GAA  CCT       288
Pro  Ser  Val  Lys  Lys  Ser  Ser  Gln  Phe  His  Leu  Arg  Val  Ile  Glu  Pro
                85                       90                           95

CCT  CCA  ACA  CCG  TCA  GCA  TCT  TGC  TTC  TTG  ACT  GAG  GGT  GGA  AAC  ATT       336
Pro  Pro  Thr  Pro  Ser  Ala  Ser  Cys  Phe  Leu  Thr  Glu  Gly  Gly  Asn  Ile
               100                      105                     110

ACT  CTC  ACC  TGC  TCG  ATC  CCG  GAA  GGT  GAC  CCC  AAA  GAG  CTC  GAT  GAT       384
Thr  Leu  Thr  Cys  Ser  Ile  Pro  Glu  Gly  Asp  Pro  Lys  Glu  Leu  Asp  Asp
          115                      120                     125

AGT  GAC  CTA  ATA  CGG  TAT  TTG  TGG  GAA  TGT  CCG  CCA  ACA  ATA  CAG  TGT       432
Ser  Asp  Leu  Ile  Arg  Tyr  Leu  Trp  Glu  Cys  Pro  Pro  Thr  Ile  Gln  Cys
     130                      135                     140

CAC  CGT  GGC  TCG  ATT  TCA  TCT  GAA  GCC  TTT  GTC  TCA  GCG  GAA  AGT  GAT       480
His  Arg  Gly  Ser  Ile  Ser  Ser  Glu  Ala  Phe  Val  Ser  Ala  Glu  Ser  Asp
145                      150                     155                          160

CTT  TCA  GAG  ATT  GTT  CAG  TGT  ACT  GTT  AGC  AAT  CCA  TTG  TTC  AGA  ACA       528
Leu  Ser  Glu  Ile  Val  Gln  Cys  Thr  Val  Ser  Asn  Pro  Leu  Phe  Arg  Thr
               165                      170                     175

TCA  GCT  TCC  GTC  TCA  TTG  TCA  ACC  TGT  TTG  CCA  GAG  GAT  TAT  GCA  AGG       576
Ser  Ala  Ser  Val  Ser  Leu  Ser  Thr  Cys  Leu  Pro  Glu  Asp  Tyr  Ala  Arg
               180                      185                     190

CAT  AGG  TTT  TCT  GGG  ACG  TCG                                                     597
His  Arg  Phe  Ser  Gly  Thr  Ser
     195
```

( 2 ) INFORMATION FOR SEQ ID NO:36:

( i ) SEQUENCE CHARACTERISTICS:
        ( A ) LENGTH: 199 amino acids
        ( B ) TYPE: amino acid
        ( D ) TOPOLOGY: unknown ( i i ) MOLECULE TYPE: protein ( i i i ) HYPOTHETICAL: YES ( x i ) SEQUENCE DESCRIPTION: SEQ ID NO:36:

```
Val  Ser  Gln  Asp  Ile  Tyr  Gly  Ala  Met  Asn  Gly  Asn  Val  Thr  Phe  Tyr
1                   5                        10                      15

Val  Ser  Glu  Ser  Gln  Pro  Phe  Thr  Glu  Ile  Met  Trp  Lys  Lys  Gly  Lys
               20                      25                      30

Asp  Lys  Val  Val  Glu  Trp  Asp  Gln  Thr  Ser  Gly  Leu  Glu  Ala  Phe  Gln
          35                       40                      45

Ser  Phe  Lys  Asn  Arg  Val  His  Leu  Asp  Ile  Val  Ser  Gly  Asn  Leu  Thr
     50                       55                      60

Ile  Thr  Gly  Leu  Thr  Lys  Leu  Asp  Glu  Asp  Val  Tyr  Glu  Ile  Glu  Ser
65                       70                      75                           80

Pro  Ser  Val  Lys  Lys  Ser  Ser  Gln  Phe  His  Leu  Arg  Val  Ile  Glu  Pro
                85                       90                           95

Pro  Pro  Thr  Pro  Ser  Ala  Ser  Cys  Phe  Leu  Thr  Glu  Gly  Gly  Asn  Ile
               100                      105                     110
```

| | | | | | | | | | | | | | | |
|---|---|---|---|---|---|---|---|---|---|---|---|---|---|---|
| Thr | Leu | Thr<br>115 | Cys | Ser | Ile | Pro | Glu<br>120 | Gly | Asp | Pro | Lys<br>125 | Glu | Leu | Asp | Asp |
| Ser | Asp<br>130 | Leu | Ile | Arg | Tyr | Leu<br>135 | Trp | Glu | Cys | Pro | Pro<br>140 | Thr | Ile | Gln | Cys |
| His<br>145 | Arg | Gly | Ser | Ile | Ser<br>150 | Ser | Glu | Ala | Phe | Val<br>155 | Ser | Ala | Glu | Ser | Asp<br>160 |
| Leu | Ser | Gln | Asn | Val<br>165 | Gln | Cys | Ile | Val | Ser<br>170 | Asn | Pro | Leu | Phe | Arg<br>175 | Thr |
| Ser | Ala | Ser | Val<br>180 | Ser | Leu | Ser | Thr | Cys<br>185 | Leu | Pro | Glu | Asp | Tyr<br>190 | Ala | Arg |
| His | Arg | Phe<br>195 | Ser | Gly | Thr | Ser | | | | | | | | | |

(2) INFORMATION FOR SEQ ID NO:37:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: other nucleic acid
        (A) DESCRIPTION: synthetic DNA (iii) HYPOTHETICAL: NO (xi) SEQUENCE DESCRIPTION: SEQ ID NO:37:

TGGGGATCCA TGGTAAGTCA AGATATTTAT GG        32

(2) INFORMATION FOR SEQ ID NO:38:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: other nucleic acid
        (A) DESCRIPTION: synthetic DNA (iii) HYPOTHETICAL: NO (xi) SEQUENCE DESCRIPTION: SEQ ID NO:38:

CCCCTGCAGC TAGGGCCCTG AGTTTCGTTG GCT        33